United States Patent
Chien et al.

(10) Patent No.: US 6,915,679 B2
(45) Date of Patent: *Jul. 12, 2005

(54) MULTI-RESERVOIR PRESSURE CONTROL SYSTEM

(75) Inventors: Ring-Ling Chien, San Jose, CA (US); J. Wallace Parce, Palo Alto, CA (US); Andrea W. Chow, Los Altos, CA (US); Anne Kopf-Sill, Portola Valley, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 585 days.

This patent is subject to a terminal disclaimer.

(21) Appl. No.: 09/792,435

(22) Filed: Feb. 23, 2001

(65) Prior Publication Data

US 2001/0052460 A1 Dec. 20, 2001

Related U.S. Application Data

(60) Provisional application No. 60/216,793, filed on Jul. 7, 2000, and provisional application No. 60/184,390, filed on Feb. 23, 2000.

(51) Int. Cl.[7] ............................................. G01N 11/00
(52) U.S. Cl. ................... 73/54.01; 73/53.01; 422/68.1; 422/50; 422/58; 422/81; 422/82.05; 422/82.08; 422/82.09
(58) Field of Search ............................ 73/54.01, 53.01, 73/54.05; 422/68.1, 50, 58, 81, 82.05, 82.08, 82.09

(56) References Cited

U.S. PATENT DOCUMENTS

| | | | | |
|---|---|---|---|---|
| 4,390,403 A | * | 6/1983 | Batchelder | 204/547 |
| 4,908,112 A | * | 3/1990 | Pace | 210/198.2 |
| 5,126,022 A | * | 6/1992 | Soane et al. | 204/458 |
| 5,304,487 A | | 4/1994 | Wilding et al. | 435/291 |

(Continued)

FOREIGN PATENT DOCUMENTS

| | | |
|---|---|---|
| WO | WO 94/05414 | 3/1994 |
| WO | WO 97/02357 | 1/1997 |
| WO | WO 00/10015 A1 | 2/2000 |
| WO | WO 00/45172 | 8/2000 |
| WO | WO 01/06370 A1 | 6/2001 |

OTHER PUBLICATIONS

Dasgupta, Pernendu K. and Liu, Shaorong. *Electroosmosis: A Reliable Fluid Propulsion System for Flow Injection Analysis. Anal. Chem.* (1994) 66. No. 7. 1792–1798.

Manz, A., et al. *Miniaturized Total Chemical Analysis Systems: A Novel Concept for Chemical Sensing. Sensors and Actuators.* B1 (1990) 244–248.

(Continued)

*Primary Examiner*—Hezron Williams
*Assistant Examiner*—Rodney Frank
(74) *Attorney, Agent, or Firm*—Donald R. McKenna

(57) ABSTRACT

Improved microfluidic devices, systems, and methods allow selective transportation of fluids within microfluidic channels of a microfluidic network by applying, controlling, and varying pressures at a plurality of reservoirs. Modeling the microfluidic network as a series of nodes connected together by channel segments and determining the flow resistance characteristics of the channel segments may allow calculation of fluid flows through the channel segments resulting from a given pressure configuration at the reservoirs. To effect a desired flow within a particular channel or series of channels, reservoir pressures may be identified using the network model. Viscometers or other flow sensors may measure flow characteristics within the channels, and the measured flow characteristics can be used to calculate pressures to generate a desired flow. Multi-reservoir pressure modulator and pressure controller systems can optionally be used in conjunction with electrokinetic or other fluid transport mechanisms.

22 Claims, 24 Drawing Sheets

U.S. PATENT DOCUMENTS

| | | | |
|---|---|---|---|
| 5,573,651 A | 11/1996 | Dasgupta et al. | 204/601 |
| 5,858,195 A | 1/1999 | Ramsey | 204/601 |
| 5,863,801 A | 1/1999 | Southgate et al. | |
| 5,885,470 A | 3/1999 | Parce et al. | |
| 5,942,443 A | 8/1999 | Parce et al. | 436/514 |
| 5,965,001 A | 10/1999 | Chow et al. | 204/600 |
| 5,979,868 A | 11/1999 | Wu et al. | 251/149.6 |
| 6,001,229 A | 12/1999 | Ramsey | 204/451 |
| 6,062,261 A | 5/2000 | Jacobson et al. | 137/827 |
| 6,110,343 A | 8/2000 | Ramsey et al. | |
| 6,134,950 A | 10/2000 | Foster et al. | |
| 6,149,787 A | 11/2000 | Chow et al. | 204/451 |
| 6,156,181 A | 12/2000 | Parce et al. | 204/600 |
| 6,231,737 B1 | 5/2001 | Ramsey et al. | 204/451 |
| 6,235,175 B1 | 5/2001 | Dubrow et al. | 204/453 |
| 6,235,471 B1 | 5/2001 | Knapp et al. | |
| 6,267,858 B1 | 7/2001 | Parce et al. | |
| 6,458,259 B1 * | 10/2002 | Parce et al. | 204/454 |
| 6,506,609 B1 * | 1/2003 | Wada et al. | 436/148 |
| 6,592,821 B1 * | 7/2003 | Wada et al. | 422/68.1 |
| 6,649,358 B1 * | 11/2003 | Parce et al. | 435/7.2 |

OTHER PUBLICATIONS

Jacobson, Stephen C., et al. *Effects of Injection Schemes and Column Geometry on the Performance of Microchip Electrophoresis Devices.* Anal. Chem. (1994) 66. No. 7. 1107–1113.

Sandoval, Junior E. and Chen, Chiaw–Min. *Method for the Accelerated Measurement of Electroosmosis in Chemically Modified Tubes for Capillary Electrophoresis.* Anal. Chem. (1996) 68. No. 17. 2771–2775.

Chien, Ring–Ling et al. *Multiport Flow–Control System for Lab–On–A–Chip Microfluidic Devices* Fresenius J. Anal. Chem. (Jul. 2001), 371:106–111.

Gambos and Forester (1998) "An Optical Micro–fluidic Viscometer." *Micro–Mechanical System* 68:187–191.

* cited by examiner

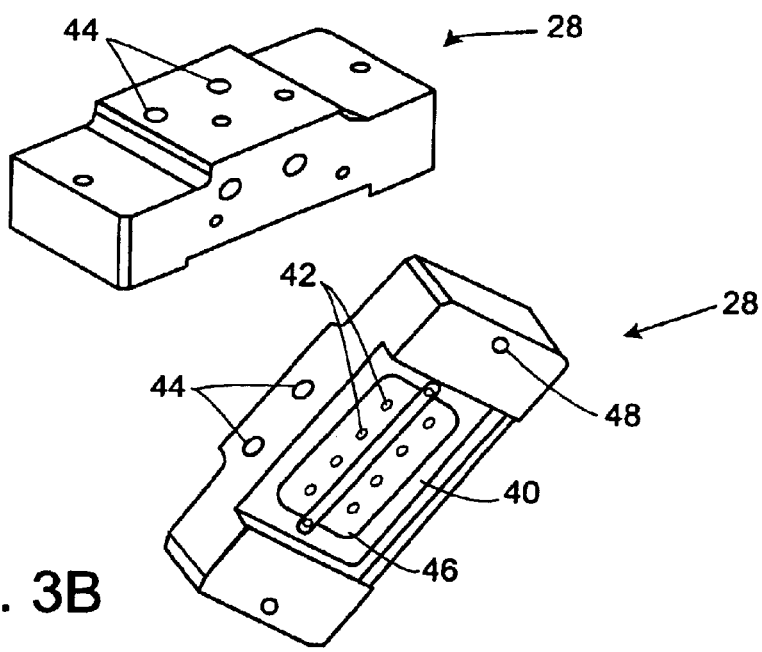
Fig. 3A
Fig. 3B
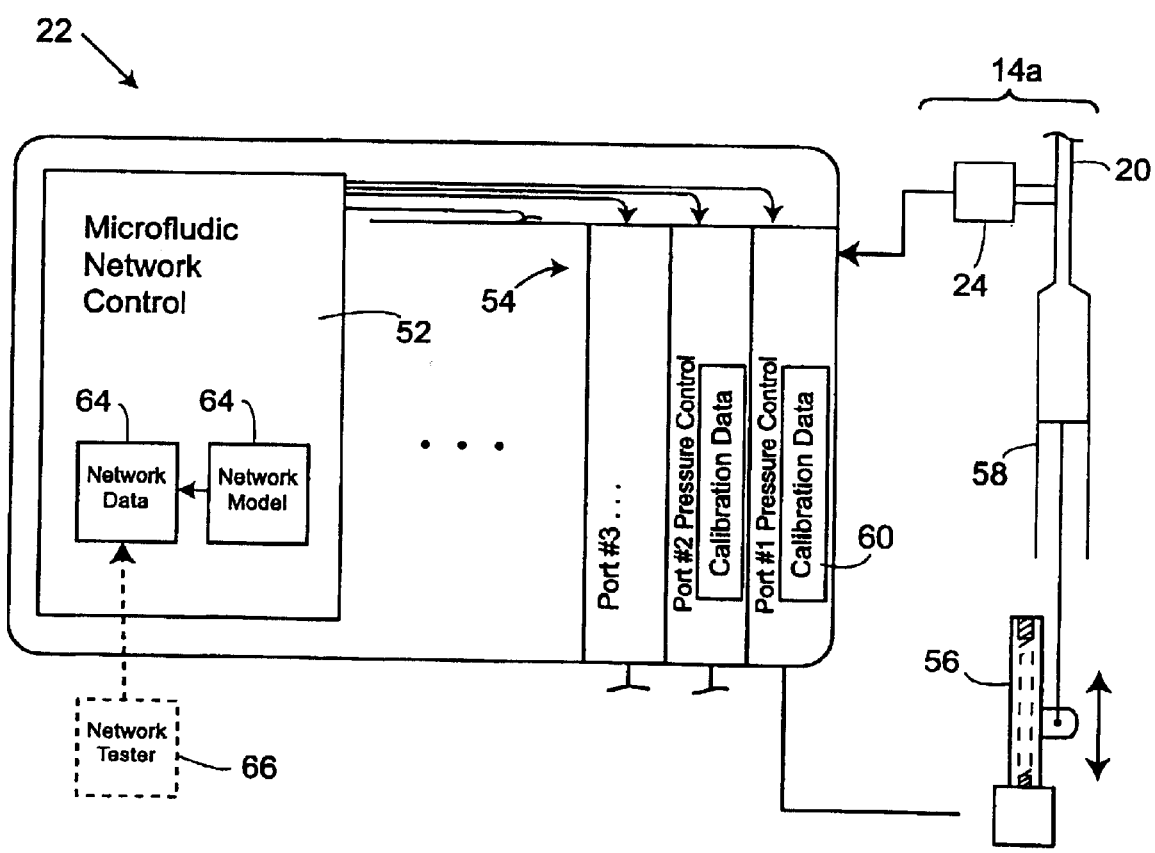
Fig. 4

MULTI-RESERVOIR PRESSURE CONTROL SYSTEM

CROSS-REFERENCES TO RELATED APPLICATIONS

The subject matter of the present application is related to that of U.S. Provisional Patent Application No. 60/184,390 filed Feb. 23, 2000, and to that of Provisional Patent Application No. 60/216,793 filed on Jul. 7, 2000, the full disclosures of which are incorporated herein by reference.

BACKGROUND OF THE INVENTION

The present invention is generally related to analytical tools for the biological and chemical sciences, and in particular, provides microfluidic devices, systems, and methods for selectively transporting fluids within microfluidic channels of a microfluidic network, often using a plurality of selectively variable pressures.

Microfluidic systems are now in use for the acquisition of chemical and biological information. These microfluidic systems are often fabricated using techniques commonly associated with the semiconductor electronics industry, such as photolithography, wet chemical etching, and the like. As used herein, "microfluidic" means a system or device having channels and chambers which are at the micron or submicron scale, e.g., having at least one cross-sectional dimension in a range from about 0.1 $\mu$m to about 500 $\mu$m.

Applications for microfluidic systems are myriad. Microfluidic systems have been proposed for capillary electrophoresis, liquid chromatography, flow injection analysis, and chemical reaction and synthesis. Microfluidic systems also have wide ranging applications in rapidly assaying compounds for their effects on various chemical, and preferably, biochemical systems. These interactions include the full range of catabolic and anabolic reactions which occur in living systems, including enzymatic, binding, signaling, and other reactions.

A variety of methods have been described to effect the transport of fluids between: a pair of reservoirs within a microfluidic system or device. Incorporation of mechanical micro pumps and valves within a microfluidic device has been described to move the fluids within a microfluidic channel. The use of acoustic energy to move fluid samples within a device by the effects of acoustic streaming has been proposed, along with the use of external pumps to directly force liquids through microfluidic channels.

The capabilities and use of microfluidic systems advanced significantly with the advent of electrokinetics: the use of electrical fields (and the resulting electrokinetic forces) to move fluid materials through the channels of a microfluidic system. Electrokinetic forces have the advantages of direct control, fast response, and simplicity, and allow fluid materials to be selectively moved through a complex network of channels so as to provide a wide variety of chemical and biochemical analyses. An exemplary electrokinetic system providing variable control of electro-osmotic and/or electrophoretic forces within a fluid-containing structure is described in U.S. Pat. No. 5,965,001, the full disclosure of which is incorporated herein by reference.

Despite the above-described advancements in the field of microfluidics, as with all successes, still further improvements are desirable. For example, while electrokinetic material transport systems provide many benefits in the microscale movement, mixing, and aliquoting of fluids, the application of electrical fields can have detrimental effects in some instances. In the case of charged reagents, electrical fields can cause electrophoretic biasing of material volumes, e.g., highly charged materials moving to the front or back of a fluid volume. Where transporting cellular material is desired, elevated electrical fields can, in some cases, result in a perforation or electroporation of the cells, which may effect their ultimate use in the system.

To mitigate the difficulties of electrokinetic systems, simplified transport systems for time domain multiplexing of reagents has been described in WO 00/45172 (assigned to the assignee of the present invention), the full disclosure of which is incorporated herein by reference. In this exemplary time domain multiplexing system, structural characteristics of channels carrying reagents can, at least in part, regulate the timing and amount of reagent additions to reactions (rather than relying solely on the specific times at which pumps are turned on and/or valves are actuated to regulate when and how much of a particular reagent is added to a reaction). While other solutions to the disadvantageous aspects of electrokinetic material transport within a microfluidic system have been described, still further alternative fluid transport mechanisms and control methodologies would be advantageous to enhance the flexibility and capabilities of known microfluidic systems.

Regardless of the mechanism used to effect movement of fluid and other materials within a microfluidic channel network, accuracy and repeatability of specific flows can be problematic. There may be variations in, for example, electroosmotic flow between two chips having similar designs, and even between different operations run on a single chip at different times. Quality control can be more challenging in light of this variability, as accurate control over microfluidic flows in applications such as high throughput screening would benefit significantly from stable and reliable assays.

In light of the above, it would be advantageous to provide improved microfluidic devices, systems, and methods for selectively transporting fluids within one or more microfluidic channels of a microfluidic network. It would be desirable if these improved transport techniques provided selective fluid movement capabilities similar to those of electrokinetic microfluidic systems, while mitigating the disadvantageous aspects of the application of electrical fields to chemical and biochemical fluids in at least some of the microfluidic channels of the network.

It would also be beneficial to provide improved devices, systems, methods and kits for enhancing the accuracy, reliability, and stability of microfluidic flows within a microfluidic network. It would be beneficial if these enhanced flow control techniques provided real-time and/or quality control feedback on the actual flows, ideally without relying on significantly increased system complexity or cost.

SUMMARY OF THE INVENTION

The present invention generally provides improved microfluidic devices, systems, and methods. The devices and systems of the invention generally allow flexible and selective transportation of fluids within microfluidic channels of a microfluidic network by applying, controlling, and varying pressures at a plurality of reservoirs or ports. By modeling the microfluidic network as a series of nodes (including the reservoirs, channel intersections, and the like) connected together by channel segments, and by determining the flow resistance characteristics of the channel segments, the fluid flows through the channel segments resulting from a given pressure configuration at the reservoirs can be determined. Reservoir pressures to effect a desired flow profile may also be calculated using the network model. A simple multi-reservoir pressure modulator and pressure controller system can optionally be used in conjunction with electrokinetic or other fluid transport mechanisms. The invention also provides techniques to avoid fluid mixture degradation within a microfluidic channel by maintaining sufficient oscillation to avoid separation of the fluid mixture when no gross movement of the fluid is desired. Microfluidic systems and methods having viscometers or other flow sensors are particularly useful for determining pressures so as to hydrodynamically induce a desire to flow in response to a measured flow within a microfluidic channel. Regardless of the mechanism used to effect movement of fluids within a microfluidic network, the techniques of the present invention may be used to provide feedback on the actual flow and/or network system characteristics, allowing (for example) more accurate, stable and reliable assays.

In a first aspect, the invention provides a microfluidic system comprising a body defining a microfluidic channel network and a plurality of reservoirs in fluid communication with the network. The network includes a channel. A plurality of pressure modulators are also included, each pressure modulator providing a selectably variable pressure. A plurality of pressure transmission lumens transmit the pressures from the pressure modulators to the reservoirs so as to induce a desired flow within the channel.

Generally, the lumens will transmit the pressures to the ports with significantly less resistance to the lumen flow than the resistance of the channel to the associated microfluidic flow. Each pressure modulator will typically be in fluid communication with an associated port via an associated lumen. In many embodiments, a network flow controller will be coupled to the pressure modulators and will send signals to the pressure modulators so that the modulators vary the pressures. The network controller will generally include channel network data which correlates the channel flows with the pressures from the pressure modulators.

In some embodiments, the network will comprise a plurality of microfluidic channels in fluid communication at channel intersections. The intersections and reservoirs will define nodes coupled by channel segments. The network data can indicate correlations between the flows in the channel segments and the plurality of pressures.

In other embodiments, a network data generator may be coupled to the network controller. The network data generator may comprise a network flow model, a viscometer coupled to the channel, and/or a network tester adapted to measure at least one parameter indicating the pressure-flow correlation. The pressure controller or controllers will often make use of signals from pressure sensors so as to provide a pressure feedback path. Optionally, the pressure controllers may include calibration data correlating drive signals with the resulting reservoir pressures. Preferably, the pressure modulators will comprise pneumatic displacement pumps.

Typically, at least one sample test liquid will be disposed in the channel network. A pressure-transmission fluid can be disposed in the lumens, with a fluid/fluid-pressure-transmission interface disposed therebetween. Typically, the pressure-transmission fluid will comprise a compressible gas, which can compliantly couple the pressure modulators with the channel flow.

Typically, the system will include at least four independently variable pressure modulators. Preferably, the system will make use of at least eight independently variable pressure modulators. A pressure interface manifold can be used to releasably engage the microfluidic body, the manifold providing sealed fluid communication between the lumens and the associated reservoirs. Ideally, a plurality of electrodes will also be coupled to the microfluidic network with an electrokinetic controller coupled to the electrodes so as to induce electrokinetic movement of fluids within the network. In general, when a hydrodynamic pressure differential is used to move fluid within the microfluidic network, the pressure differential will be significantly greater than a capillary pressure of fluids within the reservoirs.

In another aspect, the invention provides a body defining a microfluidic channel network with a plurality of reservoirs in fluid communication with the network. The network includes a first channel. A plurality of pressure modulators is also provided, with each pressure modulator in fluid communication with a reservoir for varying a pressure applied thereto. A network flow controller is coupled to the pressure modulators. The network controller comprises channel network data correlating a flow within the first channel and the pressures from the pressure modulators. The network controller independently varies the pressures from the pressure modulators in response to a desired flow within the first channel in the network data.

Optionally, the system may further include means for generating the network data coupled to the network controller. The network data generating means may comprise a model of the network, a viscometer, an electrical resistance sensor for sensing electrical resistance within the network, or the like.

In another aspect, the invention provides a microfluidic system comprising a body defining a microfluidic channel network and a plurality of ports in fluid communication with the network. The network includes a first channel. A network flow controller generates independent desired pressure signals in response to a desired flow within the first channel. A plurality of pressure modulators coupled to the network flow controller are each in fluid communication with an associated reservoir. A pressure controller with calibration data couples the pressure modulators with the network controllers. The pressure controllers transmit drive signals to the pressure modulators in response to desired pressure signals from the network flow controller and the calibration data.

In a first method aspect, the invention provides a microfluidic method comprising transmitting a first plurality of pressures to an associated plurality of reservoirs using a plurality of pressure transmission systems. A first flow is induced within a first microfluidic channel of a microfluidic network in response to the first pressures. A second plurality of pressures in determined so as to effect a desired second flow within the first microfluidic channel. The determined second plurality of pressures are applied with the pressure transmission systems and the second flow is induced within the first microfluidic channel with the second pressures.

The methods of the present invention are particularly well suited for precisely combining selected fluids within a microfluidic network, such as for multiport dilution in which concentrations of first and second fluids from first and second reservoirs can be combined at different concentrations.

In another method aspect, the invention provides a microfluidic method comprising determining pressure-induced flow characteristics of a microfluidic channel within a microfluidic network. A first plurality of pressures are derived from the characteristics of the microfluidic network so as to provide a first desired flow in a first microfluidic channel. The first desired flow is induced by applying the first pressures to a plurality of ports in communication with the microfluidic network.

In yet another method aspect, the invention provides a method for use with a fluid mixture which can degrade when held stationary. The method comprises introducing the fluid mixture into a microfluidic channel of a microfluidic network. The mixture is maintained by oscillating the fluid mixture within the channel. The maintained fluid mixture is then transported along the channel.

While analysis of the microfluidic network based on the known channel geometry can significantly facilitate calculation of pressures to be applied for generation of a desired hydrodynamic flow, work in connection with the present invention has shown that the complex nature of the flows within a microfluidic channel can make calculation of effective fluid viscosity within a microfluidic network highly problematic. Specifically, the flows within a single channel of a microfluidic network may include differing dilutions of test fluids separated by a plurality of different buffering solutions, and the like. To over come this complication, the invention often makes use of viscometers and other flow sensing systems to determine actual flow characteristics from a known microfluidic driving force. Based on these measurements, a desired flow may then be generated hydrodynamically by adjusting the appropriate reservoir pressures.

In a related method aspect, the invention provides a microfluidic method comprising inducing flow within a microfluidic channel of a microfluidic network. The flow is measured and a pressure is calculated from the measured flow so as to generate a desired flow. The desired flow is generated within the channel by applying the calculated pressure to the microfluidic network.

The flow is optionally measured by generating a detectable signal within the flow at a first location, and by measuring a time for the signal to reach a second location. The signal may comprise a change in a fluid of the flow, particularly where the first location comprises an intersection between a plurality of microfluidic channels. Such a change in the flow may be initiated hydrodynamically by applying a pressure pulse to a reservoir in communication with the intersection, and/or electrokinetically by varying an electrical field across the first intersection. Optionally, a plurality of detectable signals from a plurality of channel intersections may be sensed as each of these signals reaches the second location. In many embodiments, a signal will comprise a change in an optical quality of fluid in the flow. For example, the signal may comprise a change in a concentration of a dye from a channel intersection, as described above. Alternatively, where the fluid comprises a photobleachable dye, the dye may be photobleached by a laser at the first location with the photobleaching sensed at the second location. Many of these methods will allow a speed of the flow to be determined, particularly when a distance between the first and second locations is known. In some embodiments, the speed of the flow may be determined by, for example, Dopler velocimetry, tracer particle videography, or the like. Ideally, a viscosity of the flow can be calculated using a first pressure (which induces the measured flow) and the speed of the flow. This viscosity can then be used in determination of the calculated pressure so as to generated the desired flow.

In a related system aspect, the invention provides a microfluidic system comprising a body defining a microfluidic channel network and a plurality of reservoirs in fluid communication with the network. The network includes a microfluidic channel. A viscometer is coupled to the channel for determining a viscosity of a flow therein.

In yet another system aspect, the invention provides a microfluidic system comprising a body defining a microfluidic channel network and a plurality of reservoirs in fluid communication with the network. The network includes a microfluidic channel. A plurality of pressure modulators are in fluid communication with the reservoirs. A sensor is coupled to the channel for transmission of flow signals in response to flow within the channel. The controller couples the sensor to the pressure modulators. The controller transmits pressure commands in response to the flow signals to provide a desired flow.

In yet another aspect, the invention provides a microfluidic system comprising a body defining a microfluidic channel network and a plurality of reservoirs in fluid communication with the network. The system also includes means for selectively and independently varying pressures within the reservoirs. The pressure varying means is in fluid communication with the reservoirs.

In yet another aspect, the invention provides a microfluidic method comprising inducing a perturbation in a flow through a microfluidic channel of a microfluidic network by applying a pressure transient to the microfluidic network. A characteristic of the flow or microfluidic network is determined by monitoring progress of the perturbation.

The pressure transient may conveniently be applied by spontaneous injection of an introduced fluid into an injection channel of the microfluidic network. Such spontaneous injection may draw the introduced fluid into the injection channel using capillary forces between the injection channel and the introduced fluid.

Typically, the perturbation will comprise a change in a material of the flow downstream of an intersection. This change will often comprise a change in quantity of a fluid from a first channel, with the pressure transient being applied at the first channel.

The use of pressure induced flow perturbations may be used to determine flow or network characteristics in systems having flow that is pressure induced, electrically induced, or any mixture of flow inducing mechanisms. Typically, flow characteristics such as effective flow viscosity, flow speed, and the like may be determined. In some embodiments, network characteristics such as flow resistance of one or more channels may be determined.

The progress of the perturbation may be monitored at least in part with a sensor disposed downstream of a perturbation source location (such an intersection of channels). A speed of the flow may be determined from, for example, a time interval extending from the pressure transient to detection of the perturbation at the sensor location, and from a distance along the channel or channels extending from the source location to the sensor location. More complex analyses are also possible, such as determining a second speed of a second flow. This second speed may be generated in response to a time interval defined in part by detection of a second flow perturbation, and a second distance defined in part by a second perturbation source location (such as a second channel intersection). As the different speeds along intersecting channels may be determined, the amount of materials combined from different channels at an intersection may be calculated.

In a related system aspect, the invention provides a microfluidic system comprising a body having channel walls defining a microfluidic network. A pressure transient generator is in communication with a channel intersection of the microfluidic network for initiation of a flow perturbation. A sensor is coupled to the flow within the network at a sensor location. A processor coupled to the pressure generator and the sensor determines a characteristic of the flow or the network in response to detection of the perturbation at the sensor location.

BRIEF DESCRIPTION OF THE DRAWINGS

FIGS. 3A and 3B are perspective views of a pressure manifold for releasably sealing reservoirs of the microfluidic device of channel 2 in fluid communication with the pressure modulators of the system of FIG. 1.

FIG. 4 schematically illustrates a control system for independently varying reservoir pressures in the microfluidic system of FIG. 1.

FIG. 8 illustrates the reaction, FIG. 8A is a titration curve for different substrate concentrations, FIG. 8B is a plot of the corrected signal verses substrate concentration, FIG. 8C is a plot for determination of the Michaelis constant, and FIG. 8D is a substrate titration plot.

DESCRIPTION OF THE SPECIFIC EMBODIMENTS

Figure 1:
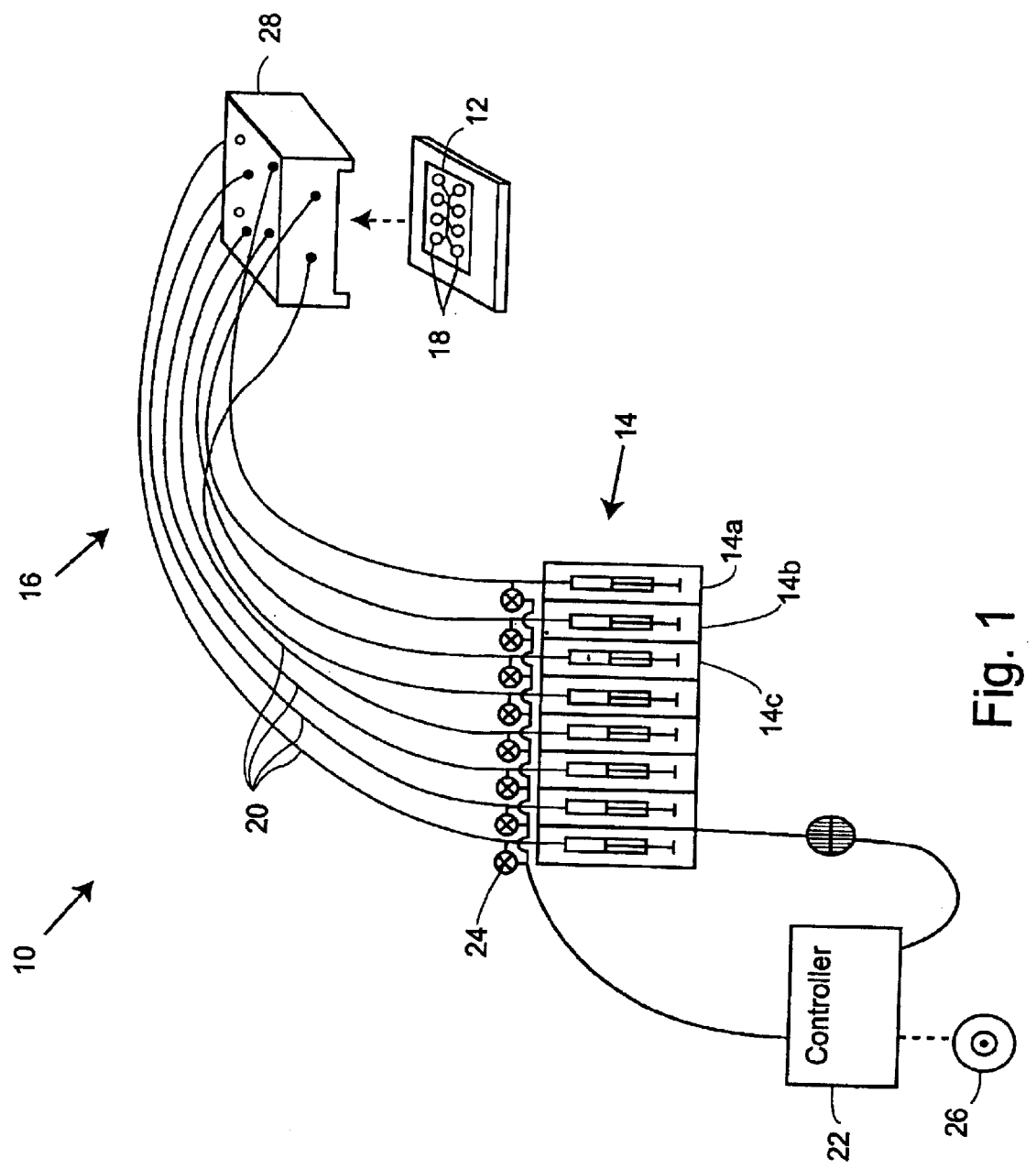
FIG. 1 schematically illustrates a microfluidic system having a multi-reservoir pressure modulation system according to the principles of the present invention.

The present invention generally makes use of a multi-reservoir pressure controller coupled to a plurality of independently variable pressure modulators to effect movement of fluids within microfluidic networks. By selectively controlling and changing the pressure applied to the reservoirs of a microfluidic device, hydrodynamic flow at very low flow rates may be accurately controlled within intersecting microfluidic channels. Such pressure-induced flows can help to decrease (or entirely avoid) any detrimental effects of the electrical fields associated with electrokinetic transportation methods, such as sample bias, cell perforation, electroporation, and the like. Additionally, such pressure-induced microfluidic flows may, through proper chip design, reduce flow variabilities as compared to electrokinetic techniques through the use of pressure differentials (and/or channel resistances that are significantly greater than flow variations induced by secondary effects, such as inflow/outflow capillary force differentials within the reservoirs). Advantageously, the pressure-induced flows of the present invention may also be combined with electrokinetic and/or other fluid transportation mechanisms thereby providing composite pressure/electrokinetic microfluidic systems.

The techniques of the present invention will often make use of data regarding the network of channels within a microfluidic device. This network data may be calculated using a model of the microfluidic network, measured by testing a microfluidic device, sensed using a sensor, and/or the like. The network data will often be in the form of hydrostatic resistances along microfluidic channel segments connecting nodes, with the nodes often being intersections between channels, ports or reservoirs, connections between channel segments having differing cross-sectional dimensions and/or flow characteristics, and the like. As used herein, the term "reservoir" encompasses ports for interfacing with a microfluidic network within a microfluidic body, including ports which do not have cross-sections that are much larger than the microfluidic channel to enhance fluid capacity.

By selectively controlling the pressure at most or all of the reservoirs of a microfluidic system, very small flow rates may be induced through selected channel segments. Such small pressure-induced flows can be accurately controlled at flow rates which might be difficult and/or impossible to control using alternative fluid transportation mechanisms. Advantageously, the present invention may provide flow rates of less than 0.1 nanoliters per second, the flow rates often being less than 1 nanoliters per second, and the pressure induced flow rates typically being less than 10 nanoliters per second within the microfluidic channel.

To accurately apply the pressures within the microfluidic network, the invention generally makes use of a pressure transmission system having relatively large lumens coupling the pressure modulators to the reservoirs of the microfluidic device, with the pressure transmission lumens ideally containing a compressible gas. Pressure is often transmitted through this relatively low resistance pressure transmission system to fluids disposed within the reservoirs of the microfluidic system via a gas/fluid interface within the reservoir. The resistance of the microfluidic channels to the fluid flows therein is typically much greater than the resistance of the pressure transmission lumens to the associated flow of compressible gas. Generally, the channel resistance is at least 10 times the transmission system resistance, preferably being at least 100 times, and ideally being at least 1000 times the transmission system resistance of the compressible gas used to induce the channel flows. In other words, a response time constant of the pressure transmission system will generally be lower than the time constant of the channel network, preferably being much lower, and ideally being at least one, two, or three orders of magnitude lower. The head space of a fluid (for example, in the pressure modulator pump and/or in the port or reservoir) times the resistance of the fluid flow (for example, in the channels or lumens) may generally define the response time constant.

Surprisingly, it is often advantageous to enhance the resistance of the microfluidic channels to provide the desired relative resistance factors. The channels may have reduced cross-sectional dimensions, pressure drop members (such as a small cross-section pressure orifice, a flow restricting substance or coating, or the like), and/or lengths of some, most, or even all of the microfluidic channel segments may be increased by including serpentine segment paths. As the resistance of the pressure transmission system can be several orders of magnitude less than the resistance of the channels, pressure differentials can be accurately transmitted from the pressure modulators to the reservoirs of the microfluidic device. Additionally, reduced transmission system resistances can help to enhance the response of the pressure system, providing a faster response time constant.

Referring now to FIG. 1, a microfluidic system 10 includes a microfluidic device 12 coupled to a bank of pressure modulators 14 by a pressure transmission system 16. Pressure modulator bank 14 includes a plurality of pressure modulators 14a, 14b, . . . Modulator bank 14 will generally include at least three independently, selectively variable pressure modulators, typically having at least four modulators, and ideally having eight or more modulators. Each modulator is in fluid communication with a reservoir 18 of microfluidic device 12 via an associated tube 20, the tube having a pressure transmission lumen with a compressible gas therein.

Modulator bank 14 generally provides independently selectable pressures to the lumens of tubing 20 under the direction of a controller(s) 22. Feedback may be provided to controller 22 from pressure sensors 24, as will be described hereinbelow. Processor 22 will often comprise a machine-readable code embodied by a tangible media 26, with the machine-readable code comprising program instructions and/or data for effecting the methods of the present invention. Processor 22 may comprise a personal computer having at least an Intel Pentium® or Pentium II® processor having a speed of at least 200 MHz, 300 MHz, or more. Tangible media 26 may comprise one or more floppy disks, compact disks, or "CDs," magnetic recording tape, a read-only memory, a random access memory, or the like. In some embodiments, the programming instructions may be input into controller 22 via a disk drive or other input/output system such as an internet, intranet, modem reservoir, or the like. Suitable programs may be written: in a variety of programming languages, including the LabView™ language, as available from National Instruments of Austin, Tex. Controller 22 transmits drive signals to modulator bank 14, ideally via an RS232/RS485 serial connection.

In addition to tubing 20, pressure transmission system 16 includes a manifold 28. Manifold 28 releasably seals the lumen of each tube 20 with an associated reservoir 18 of microfluidic device 12. Tubing 20 may comprise a relatively high-strength polymer such as polyetheretherketone (PEEK), or a polytetrafluoroethylene (such as a Teflon™ material), or the like. The tubing typically has an inner diameter in a range from about 0.01" to about 0.05", with a length from about 1 m to about 3 m. A "T" connector couples the pressure output from each pressure modulator to an associated pressure sensor 24.

Each modulator 14a, 14b . . . generally comprises a pump or other pressure source which pressurizes the compressible gas within the lumen of associated tubing 20. The modulators preferably comprise positive displacement pumps, with the exemplary modulators comprising a piston which is selectively positioned within a surrounding cylinder by an actuator. Preferably, the actuators are adapted to allow accurate positioning of the piston in response to drive signals from controller 22, the exemplary actuators comprising stepper motors. The exemplary piston/cylinder arrangement is similar to a syringe. Exemplary modulator banks may be provided by (or modified from components available through) a variety of commercial sources, including Kloehn of Las Vegas, Nev., Cavaro of Sunnyvale, Calif., and the like.

Figure 2:
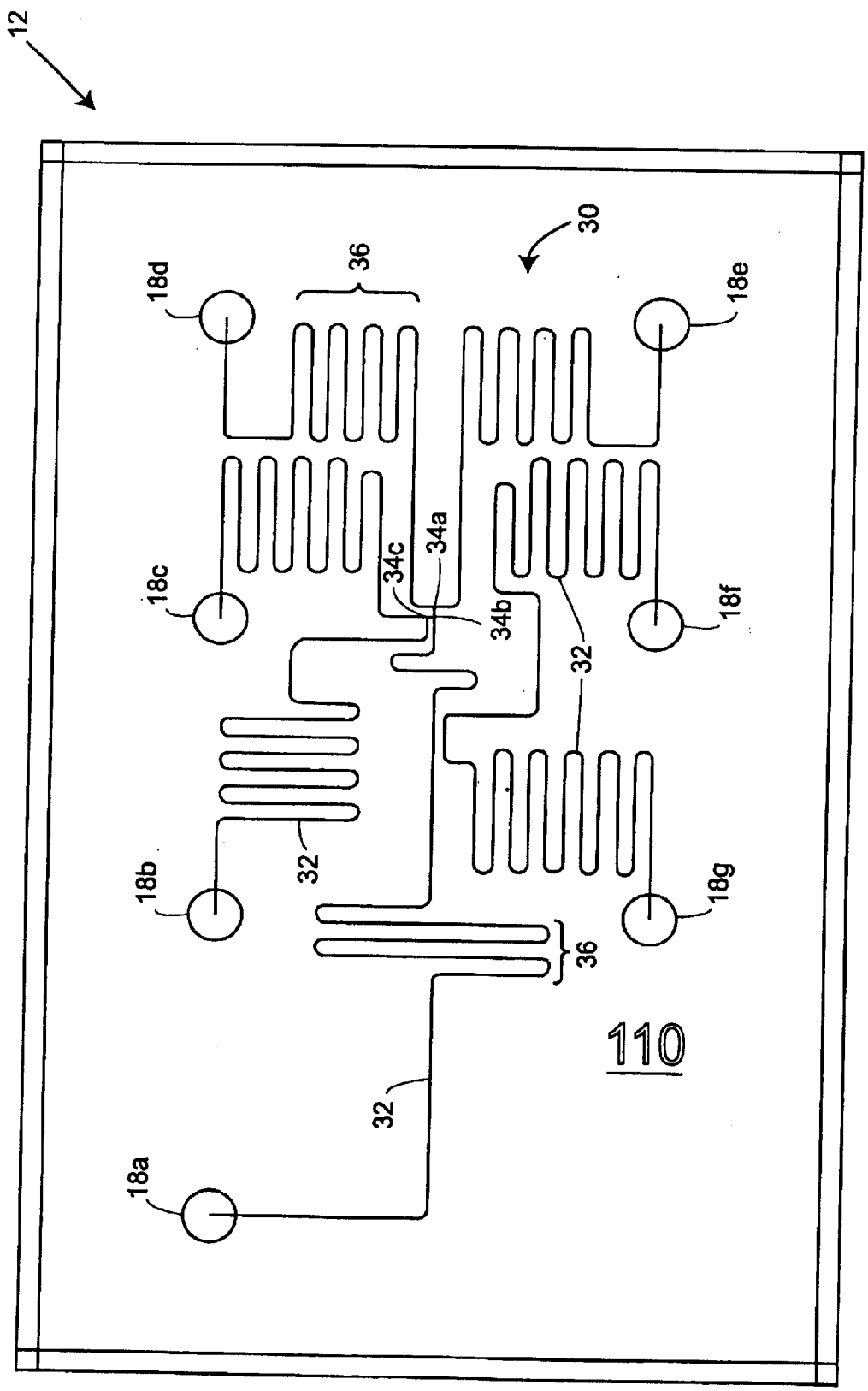
FIG. 2 is a plan view of a representative microfluidic device having microfluidic channels with enhanced fluid flow resistance for use in the microfluidic system of FIG. 1.

Microfluidic device 12 is seen more clearly in FIG. 2. Microfluidic device 12 includes an array of reservoirs 18a, 18b, . . . coupled together by microscale channels defining a microfluidic network 30. As used herein, the term "microscale" or "microfabricated" generally refers to structural elements or features of a device which have at least one fabricated dimension in the range of from about 0.1 $\mu$m to about 500 $\mu$m. Thus, a device referred to as being microfabricated or microscale will include at least one structural element or feature having such a dimension. When used to describe a fluidic element, such as a passage, chamber or conduit, the terms "microscale", "microfabricated" or "microfluidic" generally refer to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 50 $\mu$m.

The microfluidic devices or systems of the present invention typically include at least one microscale channel, usually at least two intersecting microscale channel segments, and often, three or more intersecting channel segments disposed within a single body structure. Channel intersections may exist in a number of formats, including cross intersections, "T" intersections, or any number of other structures whereby two channels are in fluid communication.

The body structures of the devices which integrate various microfluidic channels, chambers or other elements may be fabricated from a number of individual parts, which when connected form the integrated microfluidic devices described herein. For example, the body structure can be fabricated from a number of separate capillary elements, microscale chambers, and the like, all of which are connected together to define an integrated body structure. Alternatively and in preferred aspects, the integrated body structure is fabricated from two or more substrate layers which are mated together to define a body structure having the channel and chamber networks of the devices within. In particular, a desired channel network is laid out upon a typically planar surface of at least one of the two substrate layers as a series of grooves or indentations in that surface. A second substrate layer is overlaid and bonded to the first substrate layer, covering and sealing the grooves, to define the channels within the interior of the device. In order to provide fluid and/or control access to the channels of the device, a series of reservoirs or reservoirs is typically provided in at least one of the substrate layers, which reservoirs or reservoirs are in fluid communication with the various channels of the device.

A variety of different substrate materials may be used to fabricate the devices of the invention, including silica-based substrates, i.e., glass, quartz, fused silica, silicon and the like, polymeric substrates, i.e., acrylics (e.g., polymethylmethacrylate) polycarbonate, polypropylene, polystyrene, and the like. Examples of preferred polymeric substrates are described in commonly owned published international patent application no. WO 98/46438 which is incorporated herein by reference for all purposes. Silica-based substrates are generally amenable to microfabrication techniques that are well-known in the art including, e.g., photolithographic techniques, wet chemical etching, reactive ion etching (RJE) and the like. Fabrication of polymeric substrates is generally carried out using known polymer fabrication methods, e.g., injection molding, embossing, or the like. In particular, master molds or stamps are optionally created from solid substrates, such as glass, silicon, nickel electro forms, and the like, using well-known micro fabrication techniques. These techniques include photolithography followed by wet chemical etching, LIGA methods, laser ablation, thin film deposition technologies, chemical vapor deposition, and the like. These masters are then used to injection mold, cast or emboss the channel structures in the planar surface of the first substrate surface. In particularly preferred aspects, the channel or chamber structures are embossed in the planar surface of the first substrate. Methods of fabricating and bonding polymeric substrates are described in commonly owned U.S. patent application Ser. No. 09/073,710, filed May 6, 1998, and incorporated herein by reference in its entirety for all purposes.

Further preferred aspects of the microfluidic devices of the present invention are more fully described in co-pending U.S. patent application Ser. No. 09/238,467, as filed on Jan. 28, 1999 (commonly assigned with the present application), the full disclosure of which is incorporated herein by reference. These preferred aspects include, for example, a reaction zone disposed within the overall body structure of the device, a reagent or other component of an "biochemical system" (generally referring to a chemical interaction that involves molecules of the type generally found within living organisms), sensing systems for detecting and/or quantifying the results of a particular reaction (often by sensing an optical or other detectable signal of the reaction), and the like.

Referring once again to FIG. 2, reservoirs 18 will often be defined by openings in an overlaying substrate layer. Reservoirs 18 are coupled together by channels 32 of microfluidic network 30, with the channels generally being defined by indentations in an underlying layer of the substrate, as was also described above.

Microfluidic channels 32 are in fluid communication with each other at channel intersections 34a, 34b, . . . (generally referred to as intersections 34). To simplify analysis of microfluidic network 30, channels 32 may be analyzed as channel segments extending between nodes defined at reservoirs 18 and/or channel intersections 34.

To provide enhanced control over movement of fluids within microfluidic network 30 by reducing the effects of secondary hydrostatic forces (such as capillary forces within reservoirs 18), the resistance of channels 32 to flow through the microfluidic network may be enhanced. These enhanced channel resistances may be provided by having a channel length greater than the normal separation between the nodes defining the channel segment, such as by having serpentine areas 36 along the channel segments. Alternatively, a cross-sectional dimension of the channel may be decreased along at least a portion of the channel, or flow may be blocked by a flow restrictor such as a local orifice, a coating or material disposed in the channel, or the like. In general, to take advantage of the full range of flow control provided by the pressure modulators, microfluidic device 12 should be optimized for hydrodynamic flow. Flow control: is generally enhanced by providing sufficient flow resistance between each reservoir 18 and the adjacent nodes so as to allow a sufficient variation in flow rate to be achieved within the various channel segments given the dynamic operating pressure range of the pressure modulators.

Pressure manifold 28 can be seen more clearly in FIGS. 3A and 3B. Manifold 28 has at least one device engaging surface 40 for engaging microfluidic device 12, with the engagement surface having an array of pressure lumens 42 corresponding to reservoirs 18 of the device. Each of pressure lumens 42 is in fluid communication with a fitting 44 for coupling each reservoir with an associated pressure modulator via an associated tube. Sealing body 46 helps maintain a seal between the associated pressure modulator and reservoir, and manifold 28 is releasably secured to device 12 by a securing mechanism 48, which here includes openings for threaded fasteners, or the like.

Manifold 28 may comprise a polymer, a metal such as 6061-T6 aluminum, or a wide variety of alternative materials. Lumens 42 may have a dimension in a range from about 2 mm to about 3 mm. Fittings 44 optionally comprise standard ¼-28 fittings. Sealing body 46 will often comprise an elastomer such as a natural or synthetic rubber.

The pressure transmission system (including manifold 28) will preferably maintain a seal when transmitting pressures greater than atmospheric pressure (positive gauge pressures) and less than atmospheric pressure (negative gauge pressures or vacuum). The pressure transmission system and modulator bank 14 will generally be capable of applying pressure differentials which are significantly higher than hydrostatic and capillary pressures exerted by, for example, a buffer or other fluid in reservoirs 18, so as to avoid variability or noise in the pressure differential and resulting flow rates. As capillary pressures within reservoirs 18 are typically less than 1/10 of a psi, often being less than 1/100th of a psi, the system will preferably be capable of varying pressure at reservoirs 18 throughout a range of at least ½ psi, more often having a pressure range of at least 1 psi, and most often having a pressure range of at least +/−1 psig (so as to provide a 2 psi pressure differential.) Many systems will be capable of applying at least about a 5 psi pressure differential, optionally having pressure transmission capabilities so as to apply pressure anywhere throughout a range of at least about +/−5 psig.

A control system for selecting the pressures applied to reservoirs 18 is schematically illustrated in FIG. 4. Controller 22 generally includes circuitry and/or programming which allows the controller to determine reservoir pressures which will provide a desired flow within a channel of microfluidic network 30 (here schematically illustrated as microfluidic network controller 52) and also includes circuitry and/or programming to direct the modulators of modulator bank 14 to provide the desired individual reservoir pressures (here schematically illustrated as a plurality of pressure controllers 54.) It should be understood that network controller 52 and pressure controller 54 may be integrated within a single hardware and/or software system, for example, running on a single processor board, or that a wide variety of distributing process techniques might be employed. Similarly, while pressure controllers 54 are schematically illustrated here as separate pressure controllers for each modulator, a single pressure controller might be used with data sampling and/or multiplexing techniques.

In general, pressure controller 54 transmits drive signals to an actuator 56, and the actuator moves a piston of displacement pump or syringe 58 in response to the drive signals. Movement of the piston within pump 58 changes a pressure in pressure transmission system 20, and the change in pressure is sensed by pressure sensor 24. Pressure sensor 24 provides a feedback signal to the pressure controller 54, and the pressure controller will optionally make use of the feedback signal so as to tailor the drive signals and accurately position the piston.

To enhance the time response of the pressure control system, pressure controller 54 may include pressure calibration data 60. The calibration data will generally indicate a correlation between drive signals transmitted to actuator 56 and the pressure provided from the pressure modulator. Pressure calibration data 60 will preferably be determined by initially calibrating the pressure change system, ideally before initiation of testing using the microfluidic network.

Generation of calibration data 60 may be effected by transmitting a calibration drive signal to actuator 56 and sensing the pressure response using pressure sensor 24. The change of pressure from this calibration test may be stored in the program as calibration data 60. The calibration signal will typically cause a known displacement of the piston within pump 58. Using this known displacement and the measured change in pressure, the overall pressure system response may be calculated for future drive signals using the ideal gas law, $PV=nRT$ (in which P is pressure, V is the total compressible air volume, n is the number of moles of gas in the volume, R is the gas constant, and T is the temperature). Calibration may be preformed for each modulator/pressure transmission systems/reservoir (so as to accommodate varying reagent quantities within the reservoirs, and the like), or may be preformed on a single reservoir pressurization system as an estimate for calibration for all of the modulators of the system.

Once calibration data 60 has been generated, pressure controller 54 can generate drive signals for actuator 56 quite quickly in response to a desired pressure signal transmitted from network controller 52. It should be noted that these estimate will preferably accommodate the changing overall volume of the compressible gas within the system, so that the calculated change in pressure for a given displacement of the piston within pump 58 at low pressures may be different than the same displacement of the piston at high pressures (i.e., the displacement/pressure correlation plot is not linear, but curves.)

In the exemplary embodiment, actuator 56 comprises a stepper motor coupled to a linear output mechanism. Pump 58 comprises a syringe having a length of about 100 mm, and a diameter of about 20 mm. Overall response time for the system may depend on a variety of parameters, including dead volume, syringe size, and the like. Preferably, the response time will be less than about 1 sec/psi of pressure change, ideally being less than about 500 msecs/psi for a pressure change from zero to 1 psi.

Network controller 52 generally calculates the desired pressure from each pressure modulator in response to a desired flow in one or more of the channels of microfluidic network 30. Given a desired channel flow, network controller 52 derives these pressures using network data 62, with the network data typically being supplied by either a mathematical model of the microfluidic network 64 and/or a tester 66. Network data 62 will generally indicate a correlation between pressure differentials applied to reservoirs 18 and flows within the microfluidic channels.

Network model 64 preferably comprises programming to help translate desired hydrodynamic flow rates into pressures to be applied at reservoirs 18. An exemplary network model 64 generates a hydrodynamic multi-level resistance network correlating to each microfluidic network 30, as can be understood with reference to FIGS. 5A–5C.

Figure 5A:
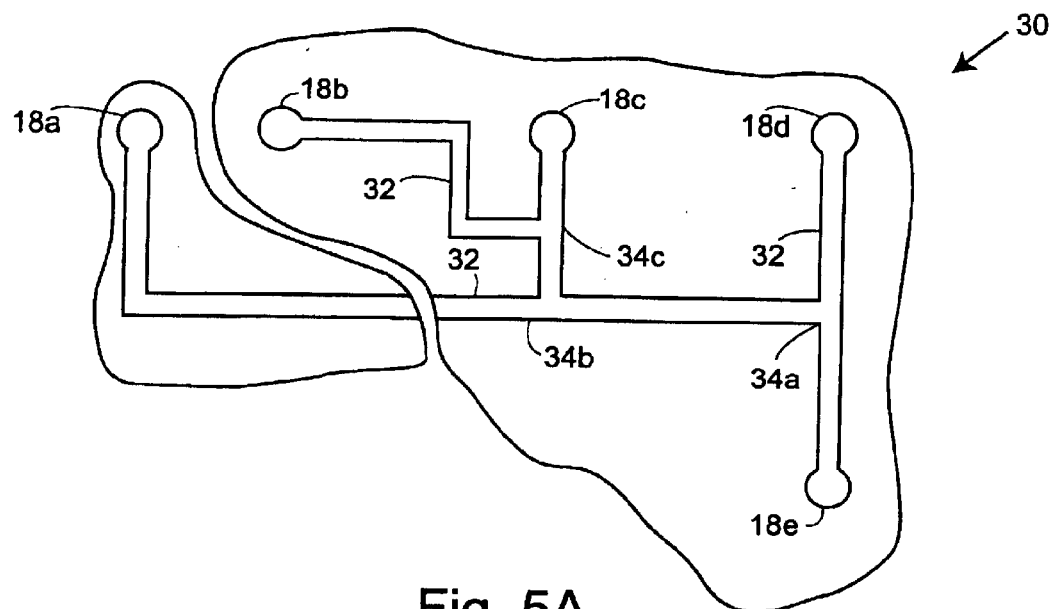
FIGS. 5A–C schematically illustrate a method and computer program for determining pressures to provide a desired flow within a channel of the microfluidic network in the microfluidic device of FIG. 2.

Referring now to FIGS. 5A and 2, nodes can be defined at each well 18 and at each intersection 34. Hydrodynamic resistances of channel segments coupling the nodes can be calculated from the chip design. More specifically, calculation of hydrodynamic resistances may be preformed using hydrostatic pressure loss calculations based on the cross sectional dimensions of channels 32, the length of channel segments connecting the nodes, the channel surface properties, the fluid properties of the fluids included in the flows, and the like.

Figure 5B:
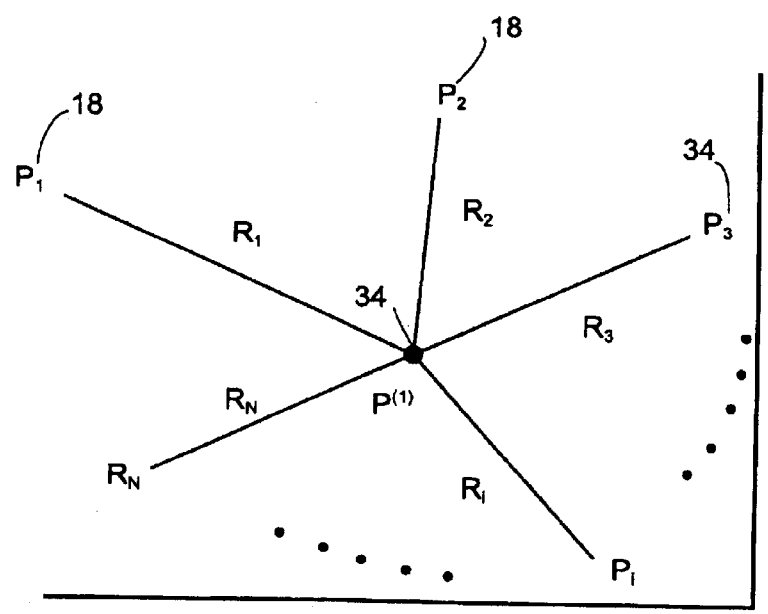
Figure 5C:
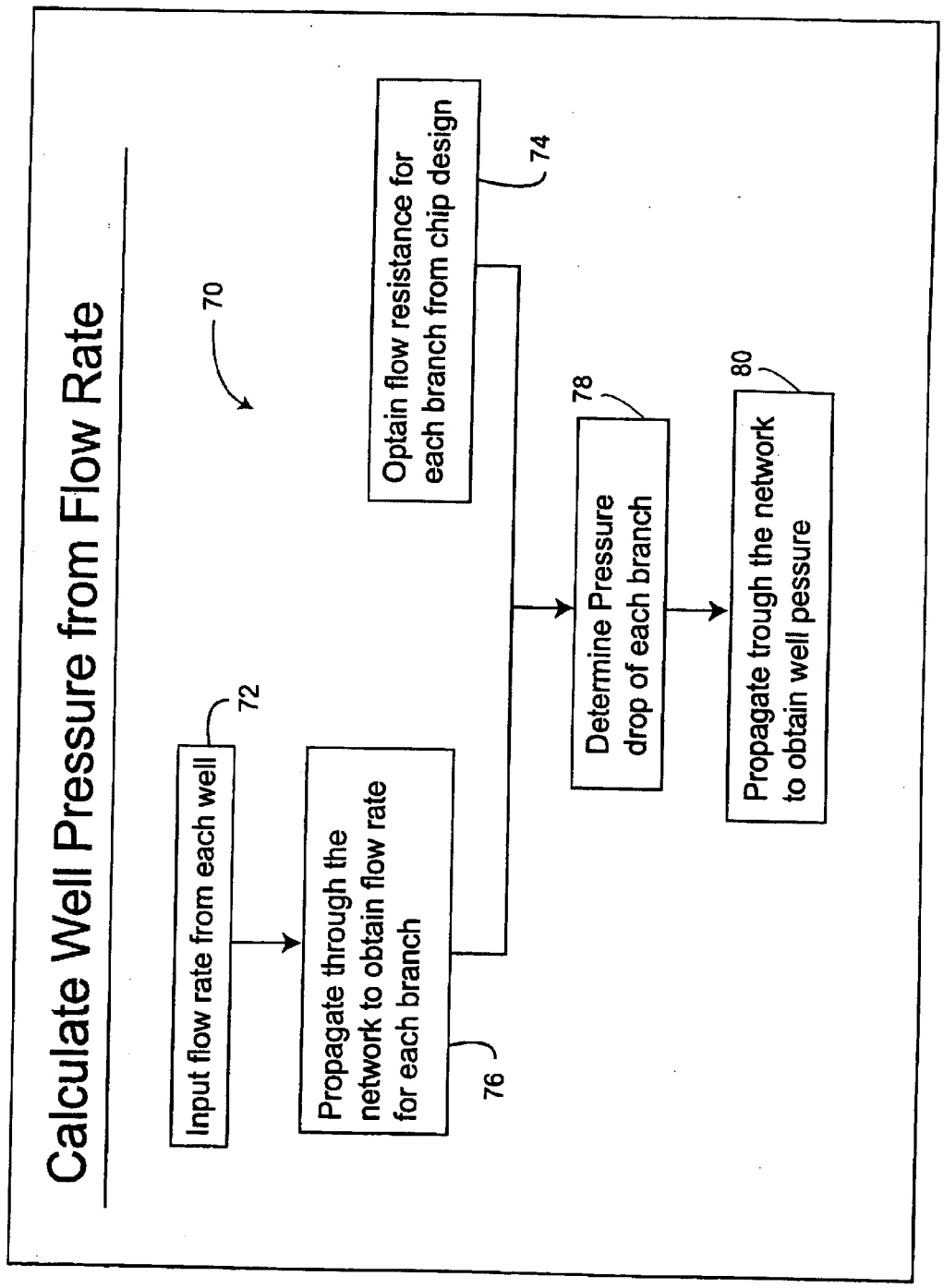

Analysis of the multi-level flow resistance network may be performed using techniques often used for analysis of current in electrical circuits, as can be understood with reference to FIGS. 5B–5C. Hydrodynamic resistances of the channel segments connecting reservoirs 18 to adjacent nodes may be analyzed as the lowest level of a multi-level network. The channel segments adjoining these lowest level segments form the second level of hydrodynamic resistances of the network. This level-by-level analysis continues until all channels of microfluidic network 30 are included in the network model. The relative flow rate of any channel in the microfluidic network can then be obtained once the flow rates from each of the reservoirs 18 in the lowest level have been calculated.

As described above, flow resistances maybe calculated based upon hydrodynamic chip design alone. It is also possible to measure these resistances using, for example, electrical sensors, pressure drop sensors, or the like. In other words, resistances to hydrodynamic flow of the channels and channel segments may be measured by, for example, measuring electrical resistance between reservoirs 18 while a conductive fluid is disposed within the network. Regardless, once the channel resistances are known, the pressure drop in each channel segment in the network can be obtained by simply multiplying the flow rate of that channel with its associated channel resistance. The pressure of each reservoir 18 can then be calculated by summing up all the pressure drops along the network 30 starting at the top level of the network.

Referring now to the exemplary program for calculating pressures illustrated in FIGS. 5D and 5C, hydrodynamic flow rate Q is related to flow resistance $R_e$ and pressure differential $\Delta P$ by the equation:

$$\Delta P = Q \cdot R_e$$

This relationship is quite similar to that used in electrokinetic calculations, in which current I and electrical resistance R are related to voltage V by the equation:

$$V = I \cdot R$$

This simplifies the application of circuit analysis techniques to the hydrodynamic analysis.

Determination of reservoir pressures so as to provide a desired flow rate will preferably be performed using a pressure calculation program 70, as illustrated in FIG. 5C. Desired flow rates are input in step 72 from each reservoir 18. These flow rates may be input by the user, by an automated test matrix generation program, or the like. Flow resistances are obtained 74 as described above, and the input flow rate propagates through the network to obtain flow rates for each branch 76. The pressure drop of each branch is then determined using the network resistance circuit 78. These pressure branches are then allowed to propagate through the network to obtain reservoir pressures 80 so as to effect the desired flow.

Figure 6:
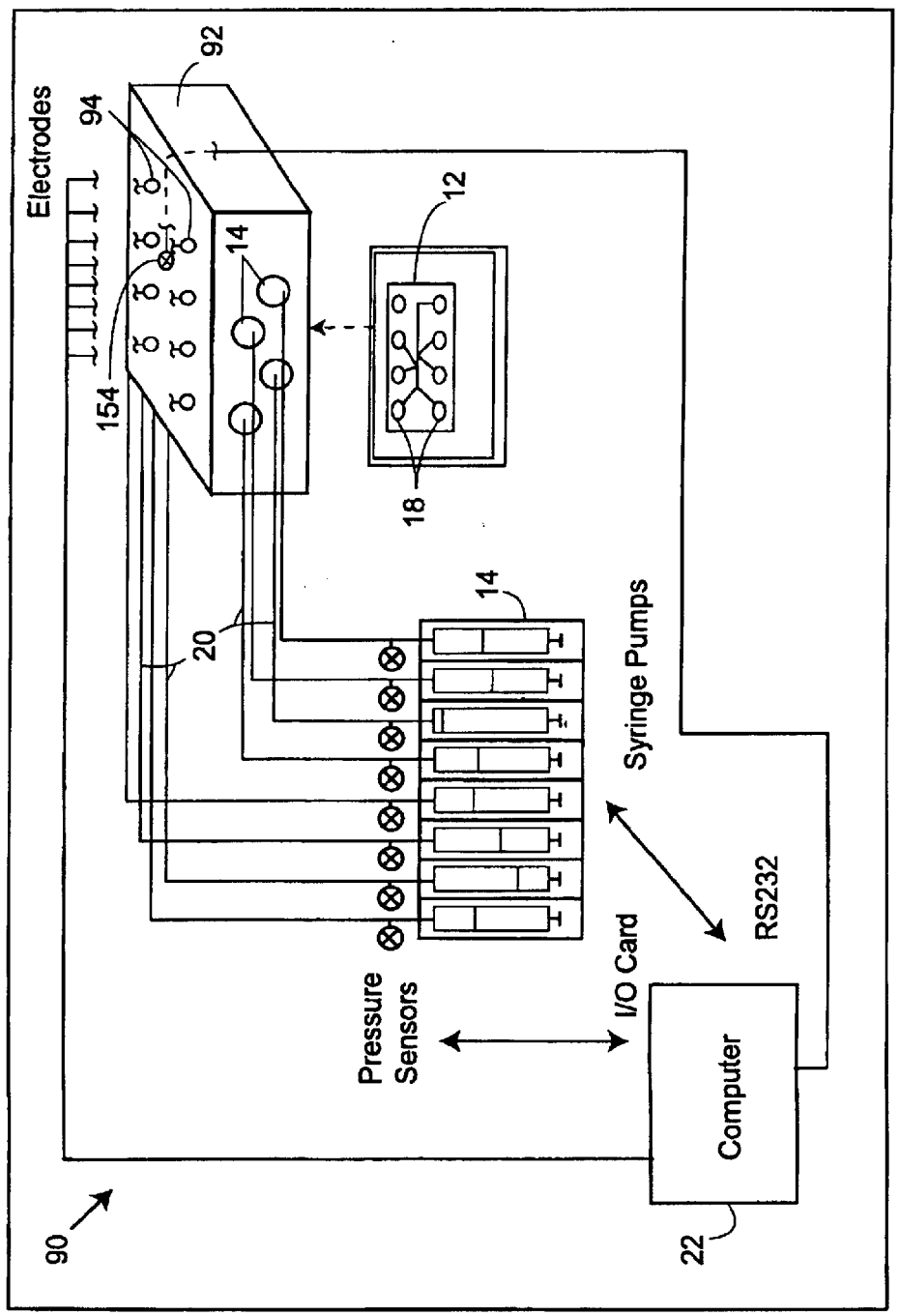
FIG. 6 schematically illustrates a microfluidic system having both a multi-reservoir pressure modulation system and an electrokinetic fluid transportation and control system according to the principles of the present invention.

Referring to FIG. 6, an alternative embodiment of a microfluidic system makes use of both electrokinetic transport and hydrodynamic transport mechanisms to move fluids within microfluidic channels of the system. Electrokinetic transfer of fluids has significant advantages when electro osmosis and/or electrophoresis are desired. Electrokinetic fluid transport is also both fast and convenient, and modifications of the channel surfaces are possible to avoid and/or eleviate electrokinetic transport disadvantages. The plug profiles of fluid plugs moved within a electrokinetic transport system can also be well-controlled and defined.

Electrokinetic/hydrodynamic system 90 also provides the advantages of hydrodynamic transport described above. This hydrodynamic transport is quite reliable, and is independent of charges and electrical surface properties of the channels. Hydrodynamic transport is particularly well-suited for biocompounds which are sensitive to electrical fields.

Electrokinetic/hydrodynamic microfluidic system 90 includes many of the pressurization, microfluidic network and control components described above. In this embodiment, manifold 92 includes fittings 44 opening laterally from the manifold to provide sealed fluid communication from each pressure transmission tube 20 to an associated reservoir 18 of the microfluidic device 12. Additionally, electrodes 94 are coupled to each reservoir 18 via manifold 92. In the exemplary embodiment, the electrodes comprise platinum surfaces which extend down from manifold 92 into electrical contact with fluids disposed within reservoirs 18 when the manifold provides a sealing engagement between fittings 44 and the reservoirs. Coupling of the electrodes with the fittings 44 may be provided by using "T" connectors within the manifold for each well, and inserting a platinum electrode across and through the "T". The appropriate (upper, in this example) connector branch of the T-connector can be sealed and the electrode affixed in place with a sealing material such as epoxy.

By coupling electrodes 94 to computer 22, and by including within computer 22 an electrokinetic fluid transport controller capable of inducing electroosmosis and electrophoresis, the system of FIG. 6 is capable of emulating pumps, valves, dispensers, reactors, separation systems, and other laboratory fluid handling mechanisms, often without having to resort to moving parts on microfluidic device 12. Electrokinetic transportation and control are described in, for example, U.S. Pat. No. 5,965,001, previously incorporated herein by reference.

Figure 7A:
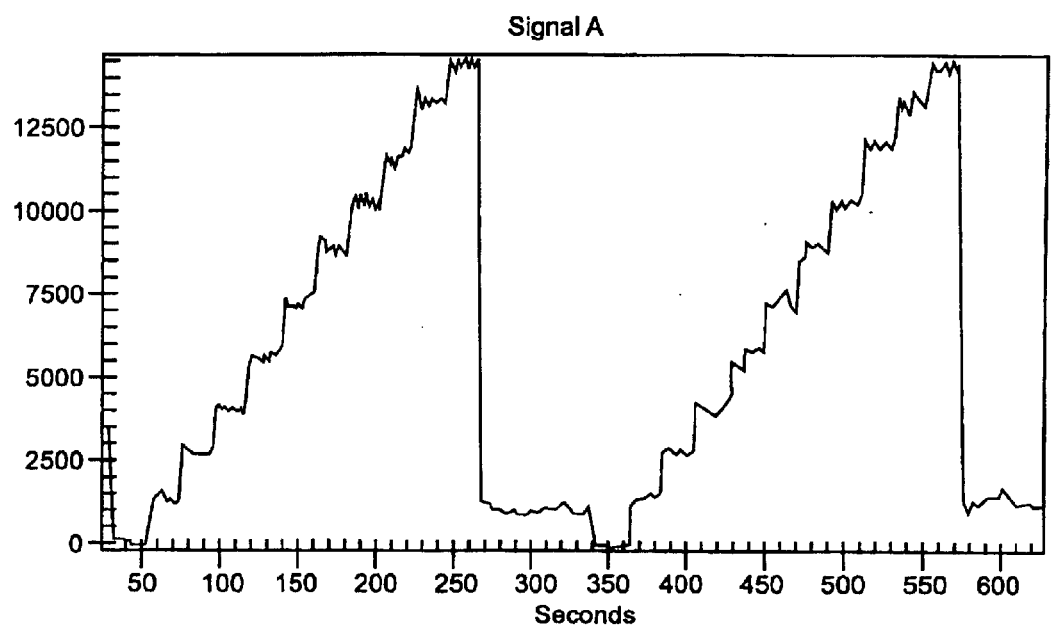
FIGS. 7A and 7B illustrate well-pair dilution in which concentration variations are produced by selectively varying the relative flow rates from two reservoirs connected at an intersection.
Figure 7B:
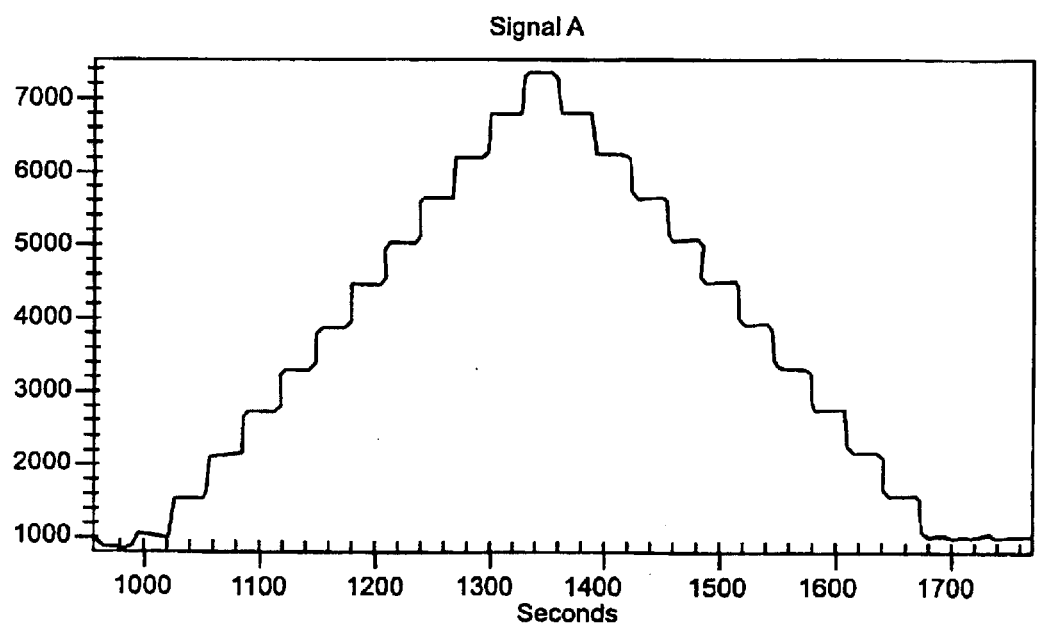

One particular advantageous use of the pressure modulated flow control can be understood with reference to FIGS. 7A and 7B. In many chemical analysis, it is desirable to vary the relative flow rates from two reservoirs connected to a common node so as to vary a concentration of a test solution, reagent, or the like, particularly for defining standard curves of chemical reactions. As illustrated in FIG. 7A, it is possible to vary the flows from two reservoirs electrokinetically, with the relative fluid concentrations being indicated by the changes in fluorescence intensity over time. Unfortunately, control over the relative flow rates (and hence, the concentration) may be less than ideal due to variation in capillary forces within the reservoirs and the like.

An alternative well-pair dilution plot in FIG. 7B can be generated by varying concentrations using multi-pressure control. This plot illustrates the reduced noise and enhanced flow control provided by the pressure control systems of the present invention. As generally described above, hydrodynamic control can be enhanced by increasing resistance of the channel segments. In the exemplary microfluidic device 12 illustrated in FIG. 2, channels 32 coupling wells 18b, 18c, 18d, 18e, 18f, and 18g to the adjacent nodes have a resistance of $1.3 \times 10^{11}$ g/cm$^4$ s. Channel 32 coupling reservoir 18a to the adjacent intersection 34 has a resistance of $4.8 \times 10^{10}$ g/cm$^4$ S. Such a chip is well-suited for use with flows having a pressure drop between reservoirs of about 2 psi, so as to provide a mixing time of about 6 seconds, and a reaction time of about 20 seconds.

Figure 7C:
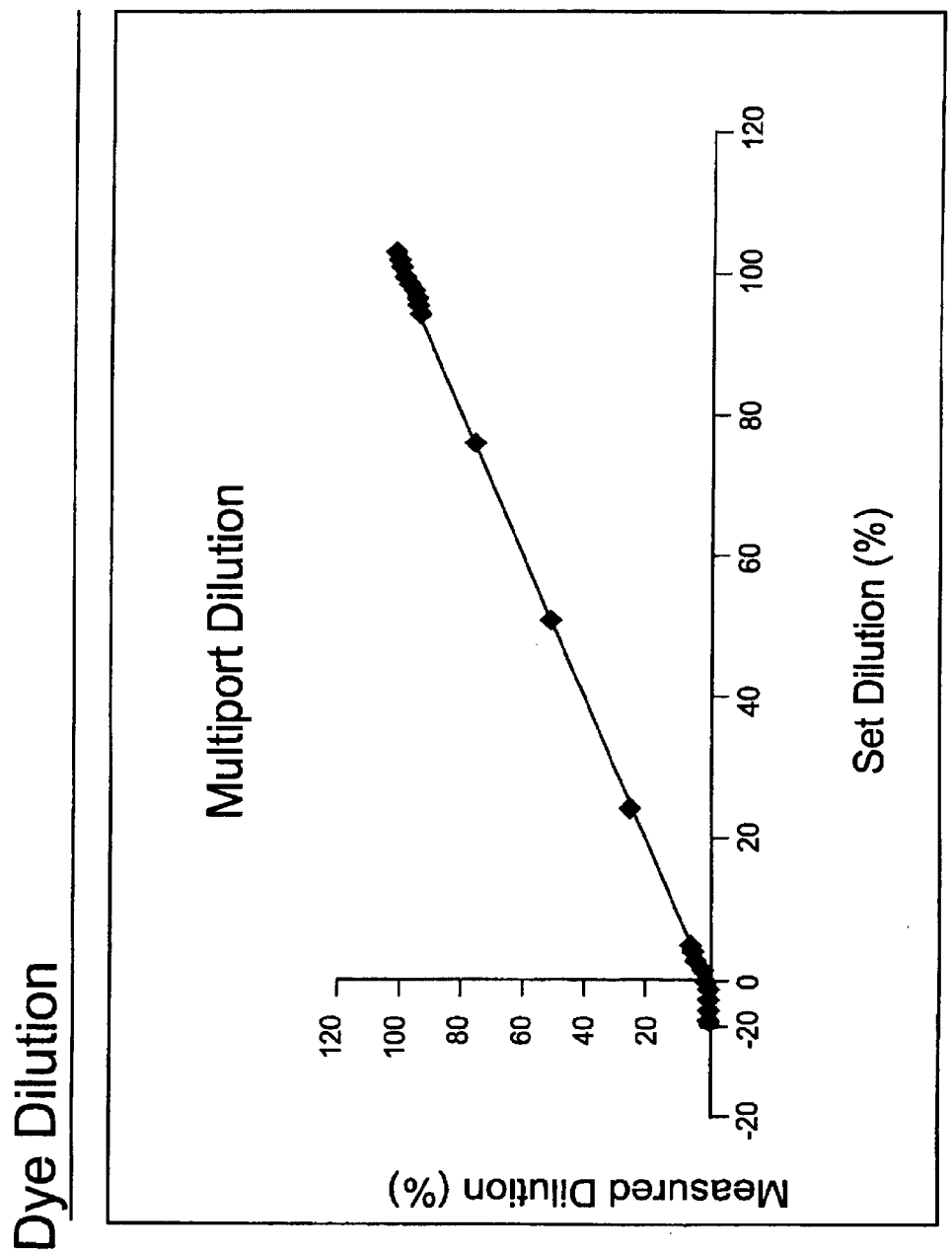
FIGS. 7C–E graphically illustrate measured dilution verses set or intended dilution for a multi-reservoir pressure controlled well-pair dilution.
Figure 7D:
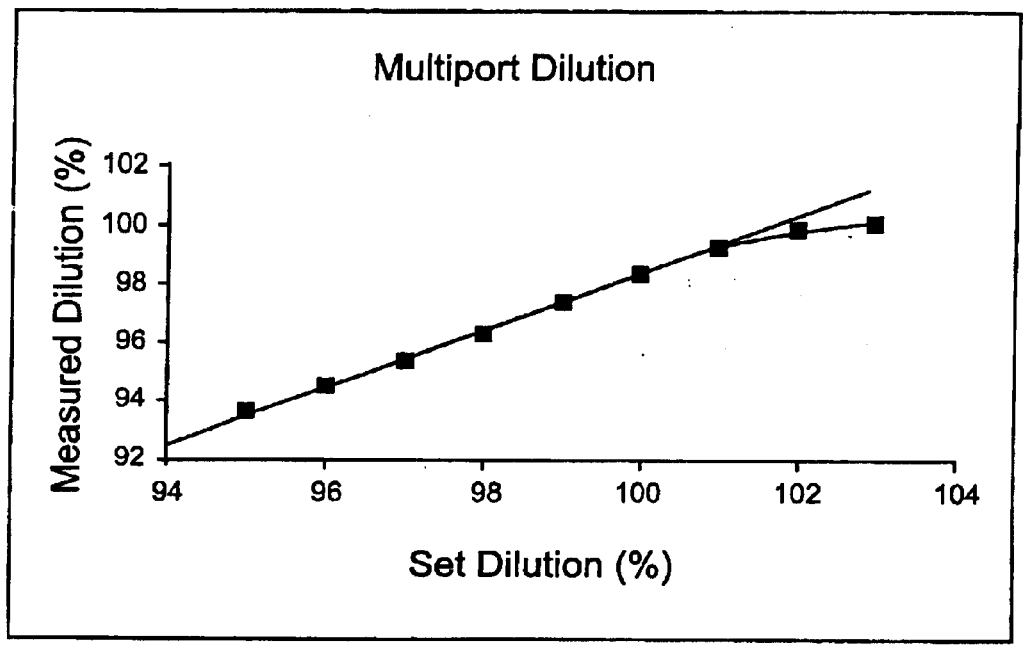
Figure 7E:
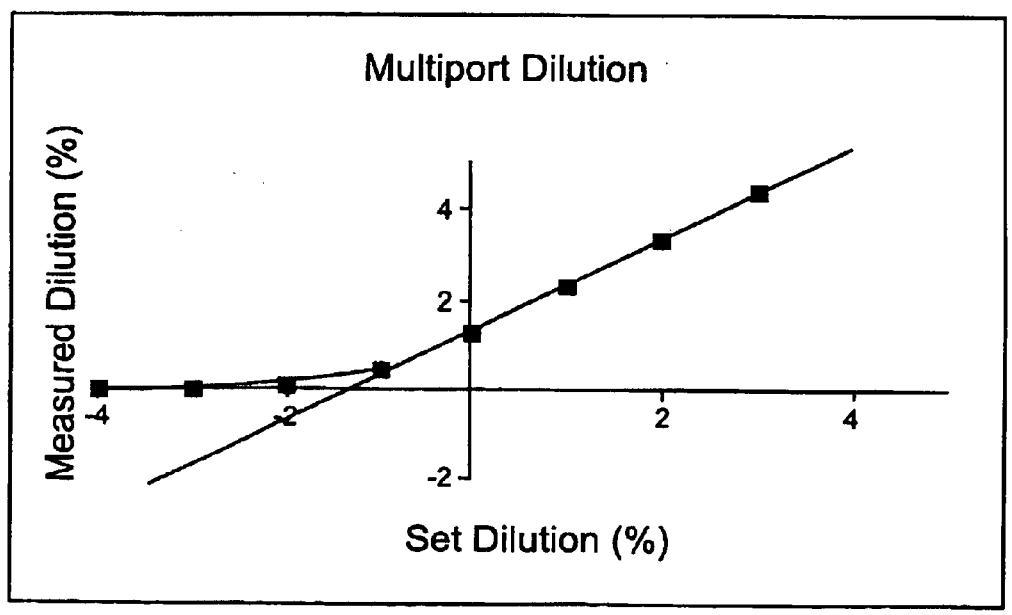

FIG. 7C is a plot of measured dilution vs. set dilution for a dilution well-pair with a hydrodynamic flow system, showing the accuracy and controllability of these dilution methods. FIGS. 7D and 7E are plots of the measured dilution near the upper and lower extremes, respectively, showing that a small amount of mixing at a channel intersection may occur when flow from a channel is at least substantially halted. As can be understood with reference to these figures, some modification of the overall flow from one or more channels at an intersection may be used to effect a desired dilution percentage adjacent a maximum and/or a minimum of the dilution range. For example, relative flow adjustments within 5% of a maximum or minimum desired dilution, and often within 2.5% of a desired maximum and/or minimum may be employed. More specifically, to achieve a near 0% actual dilution from a given channel at an intersection, fluid may flow into the channel at the intersection. Similarly, to achieve 100% measured dilution from the channel, more than 100% of the desired flow may be provided from the supply channel into the intersection.

Figure 8:
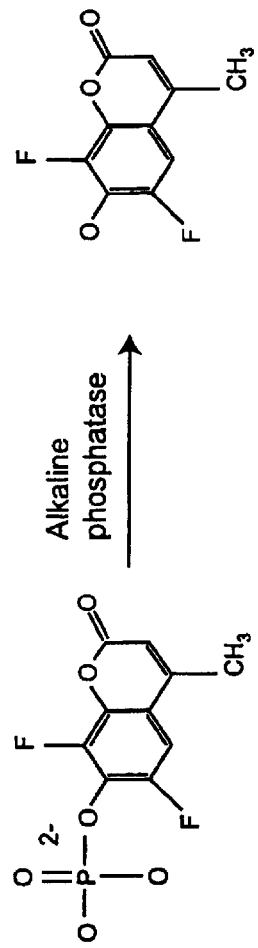
FIGS. 8 and 8A–8D graphically illustrate an enzyme assay using a multi-reservoir pressure controlled microfluidic system, and more specifically.
Figure 8A:
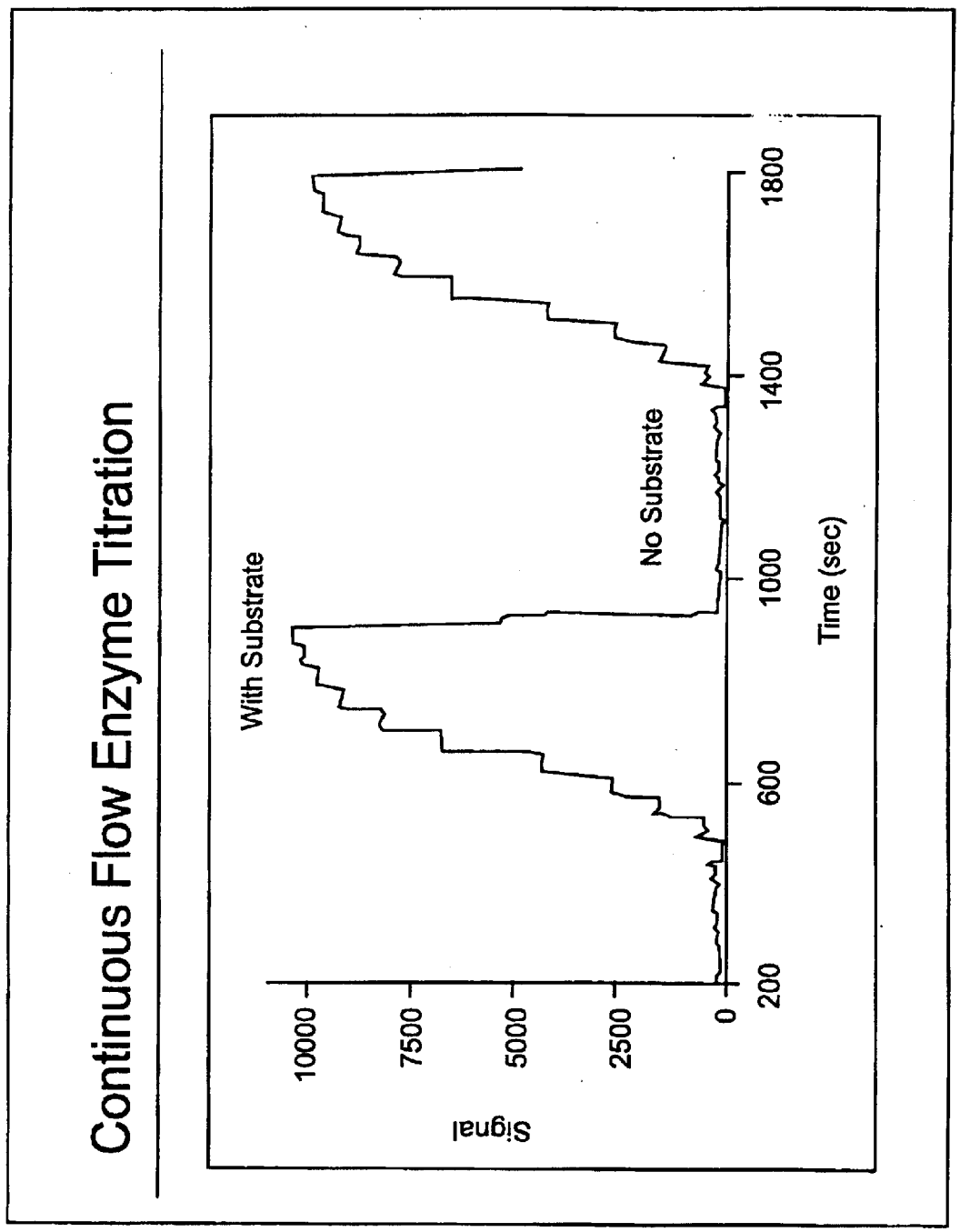
Figure 8B:
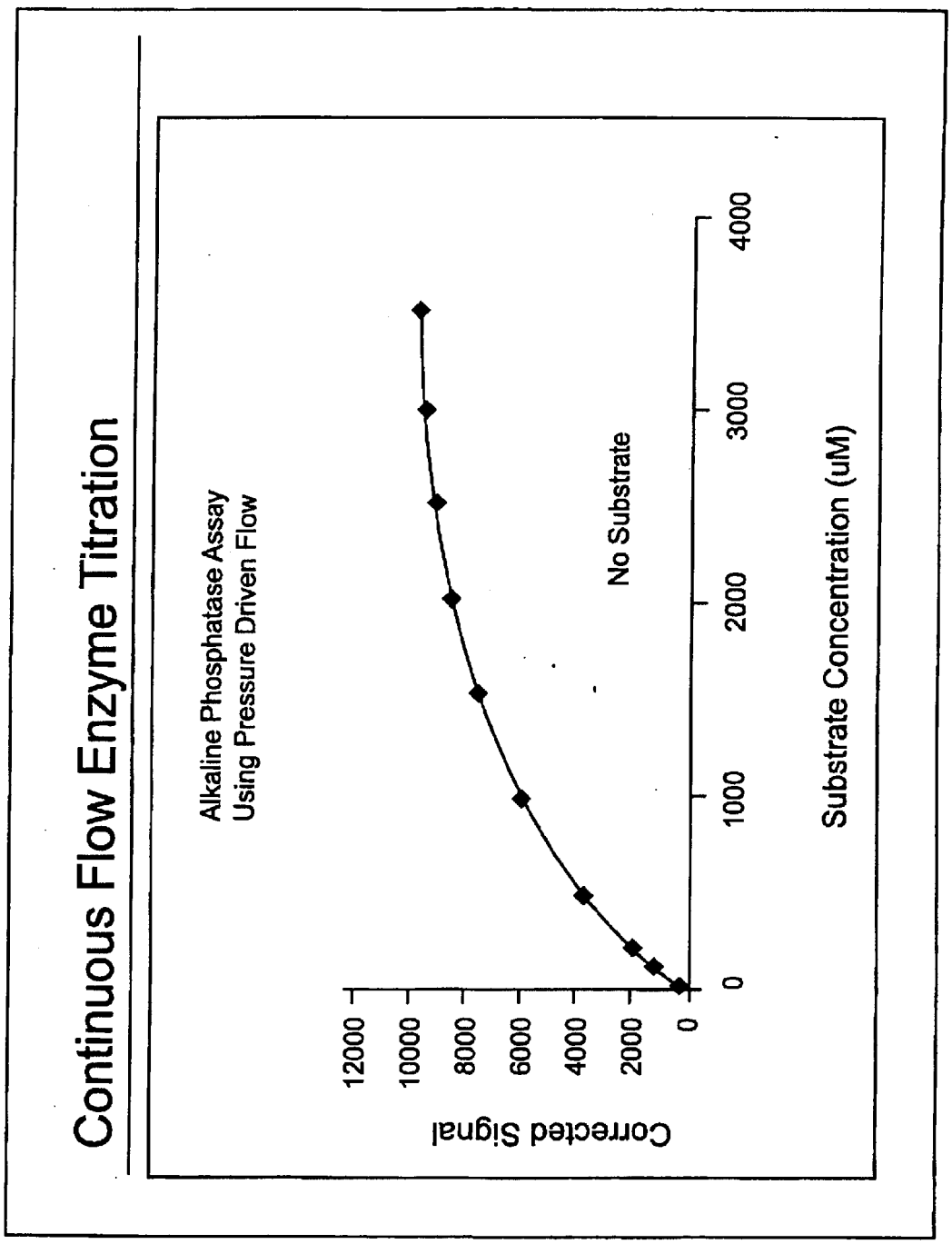
Figure 8C:
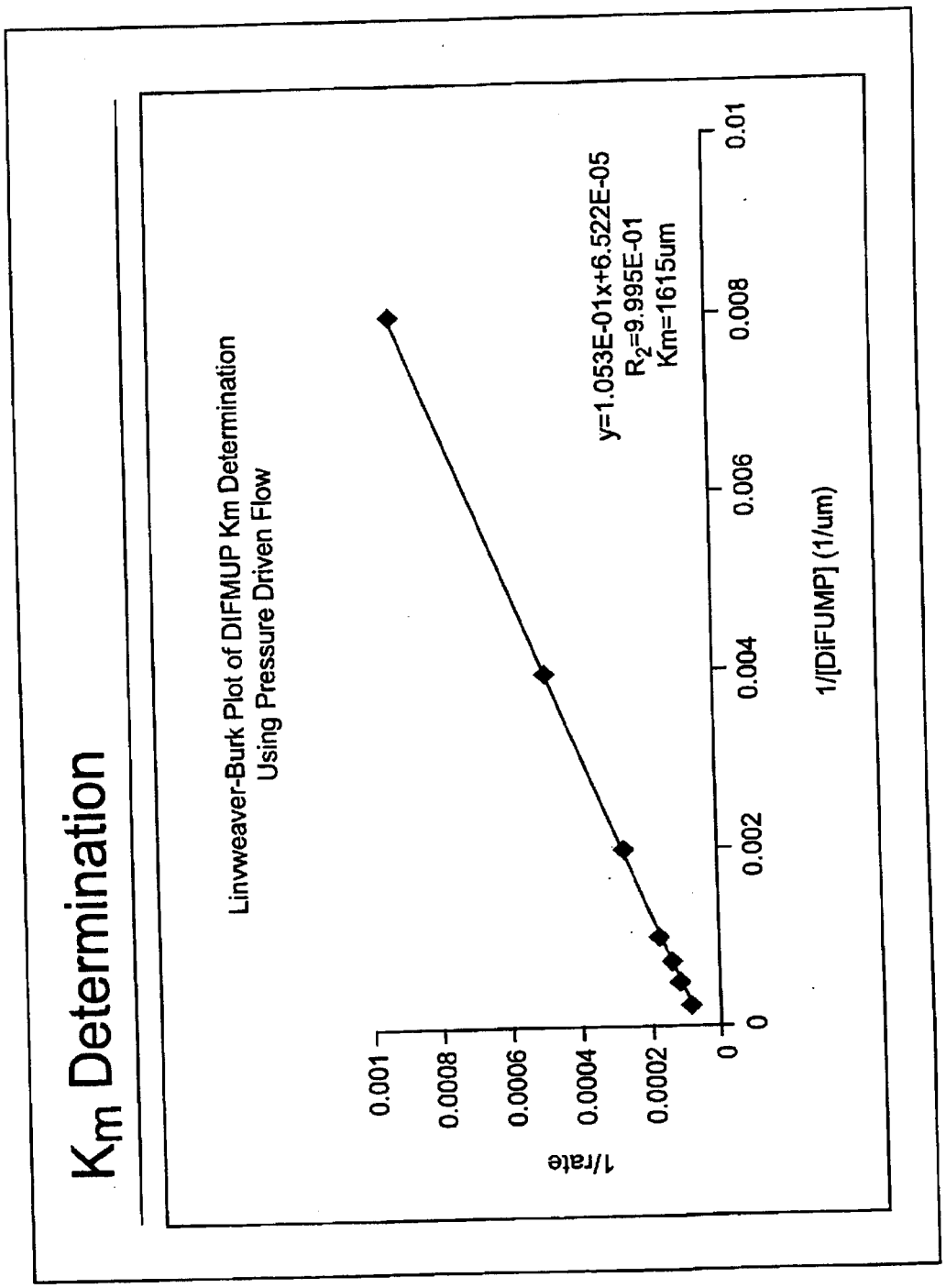
Figure 8D:
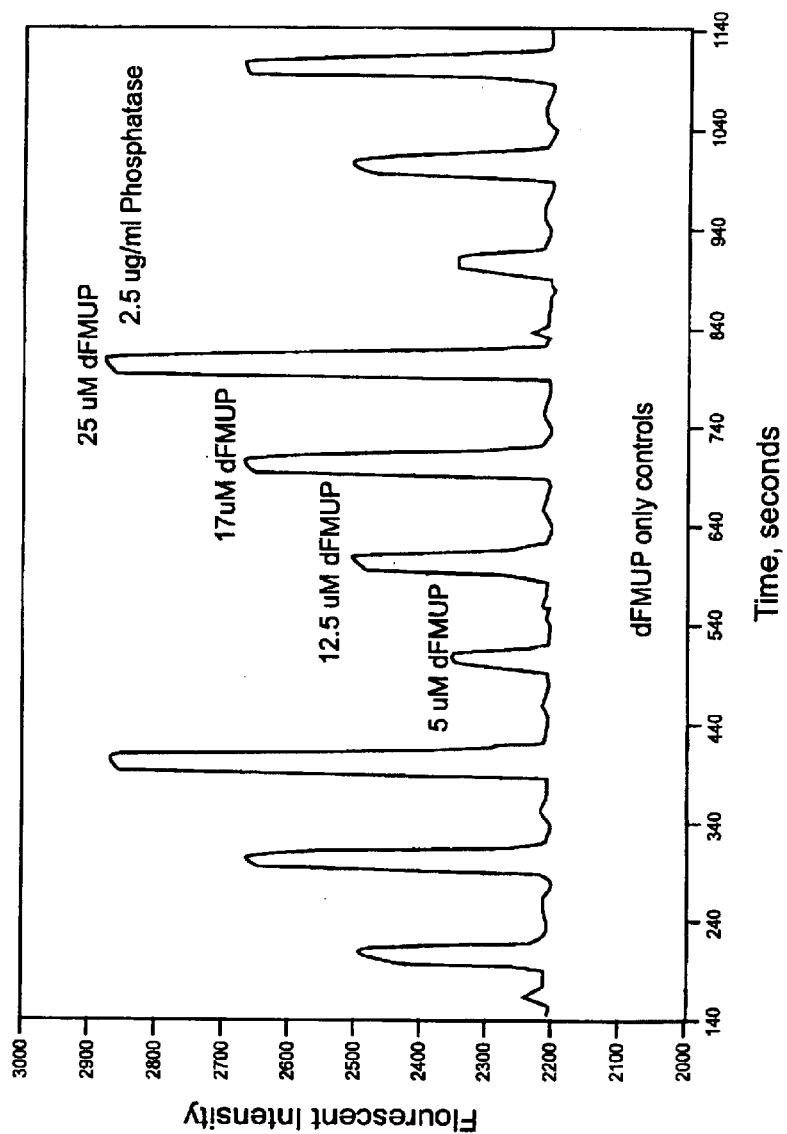

Characterization of an enzyme often involves determination of maximum reaction velocity and a Michaelis constant for each substrate. The enzymatic reaction of Alkaline Phosphatase on dFMUP (as illustrated in FIG. 8) was studied on a microfluidic device 12 optimized for pressure driven flow. FIG. 8A is a titration curve for different concentrations with and without substrate. A plot of background corrected signal vs. substrate concentration is shown in FIG. 8B, while a Lineweaver-Burk plot for the Michaelis constant (Km) is provided in FIG. 8C. Results of a substrate titration assay for the reaction are shown in FIG. 8D.

Figure 9A:
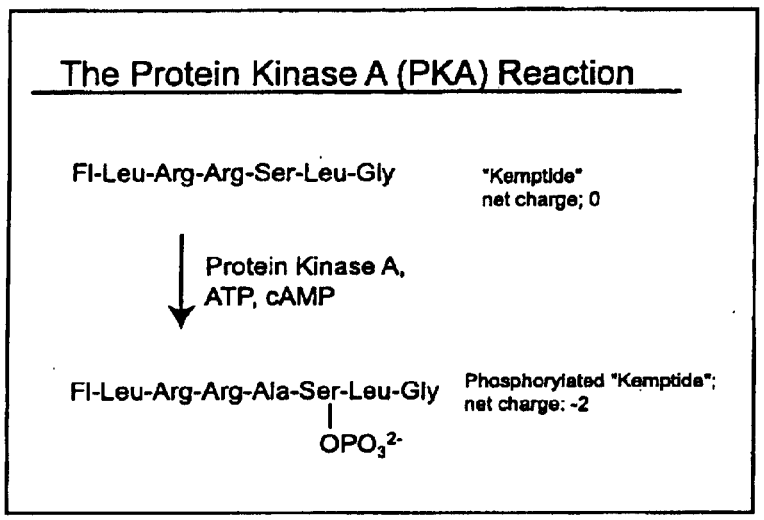
FIGS. 9A–C illustrate a microfluidic Protein Kinase A (PKA) reaction assay with variations in concentration achieved using hydrodynamic pressure modulation.
Figure 9B:
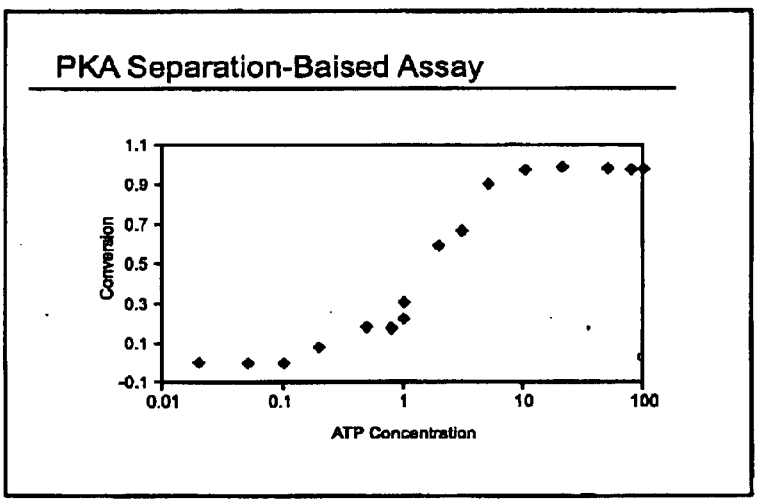
Figure 9C:
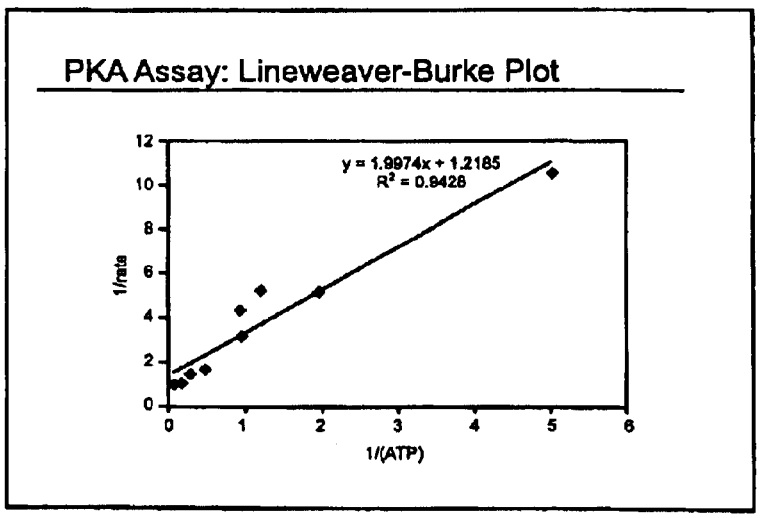
Figure 10A:
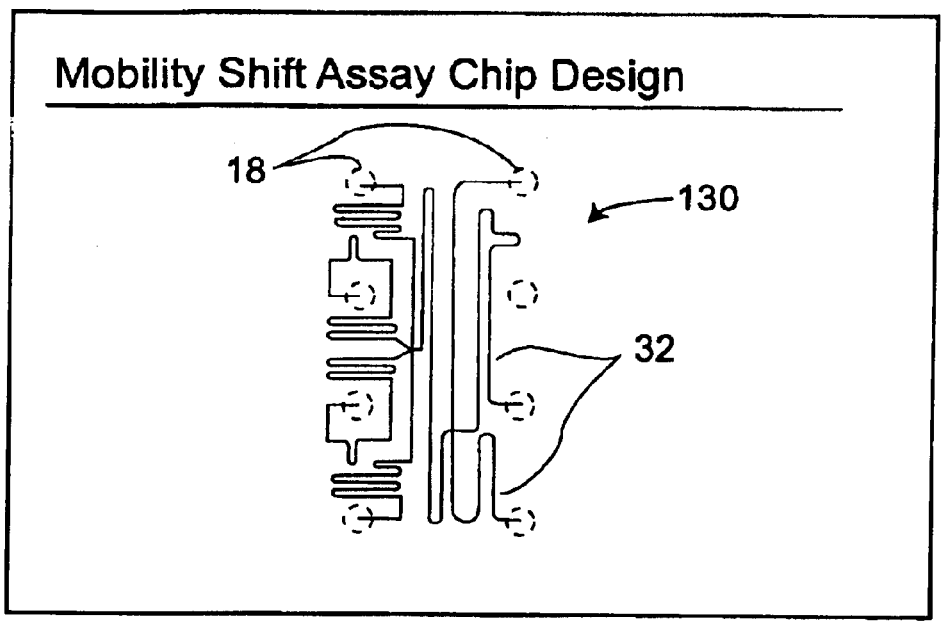
FIGS. 10A and 10B illustrate a mobility shift assay microfluidic network and assay test results at different concentrations.
Figure 10B:
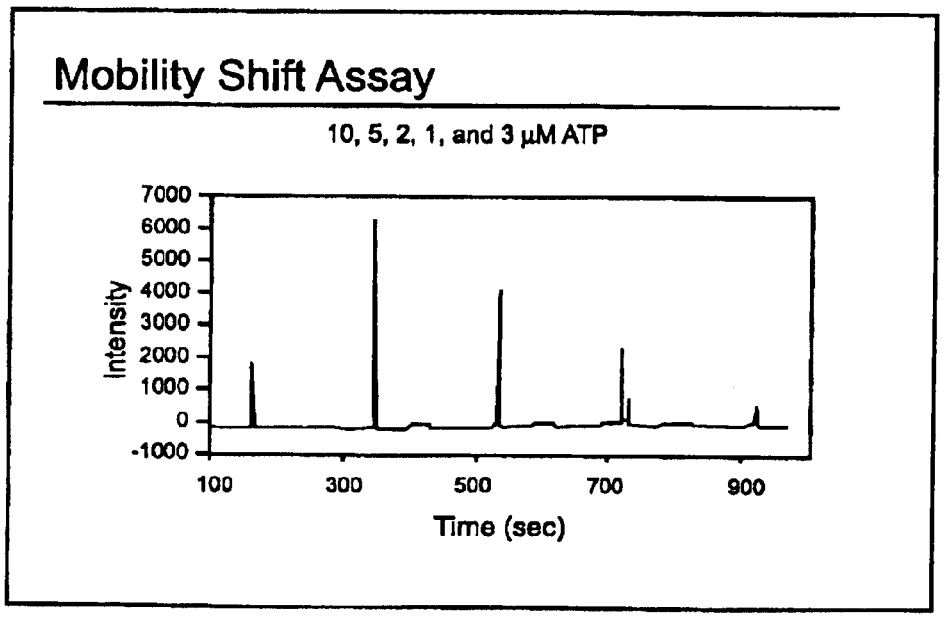

Additional exemplary assay reactions, assay results, and microfluidic networks to provide those results are illustrated in FIGS. 9A through 10B. More specifically, FIGS. 9A–C illustrate the reaction and assay results for a Protein Kinase A (PKA) assay performed at different ATP concentrations. FIG. 10A illustrates a chip design having a microfluidic network 130 of microfluidic channels 32 connecting reservoirs 18, in which the network is adapted for a mobility shift assay. FIG. 10B are exemplary results of a mobility shift assay at different concentrations of ATP as may be measured using the chip design of FIG. 10A.

Figure 11A:
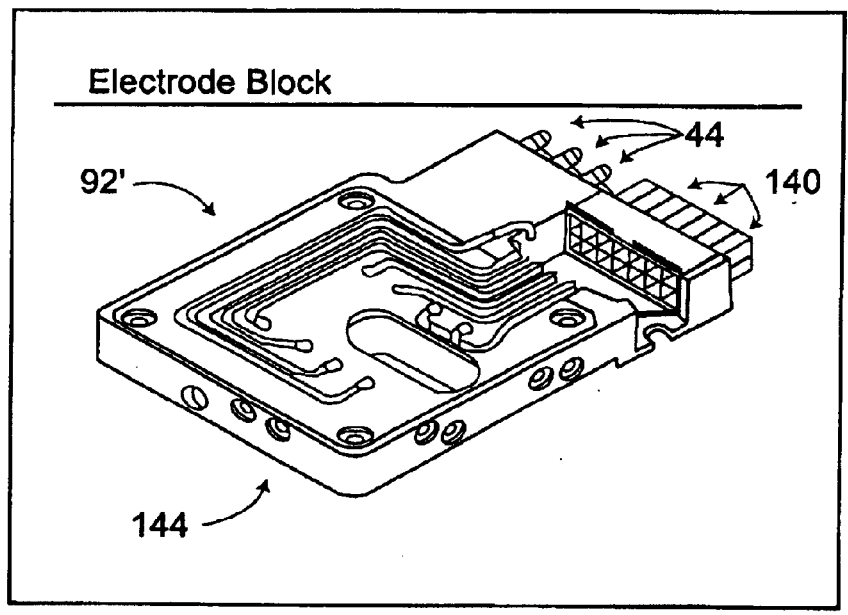
FIGS. 11A and 11B are a perspective and plane view, respectively, of an exemplary hydrodynamic and electrokinetic interface structure for coupling to a microfluidic body.
Figure 11B:
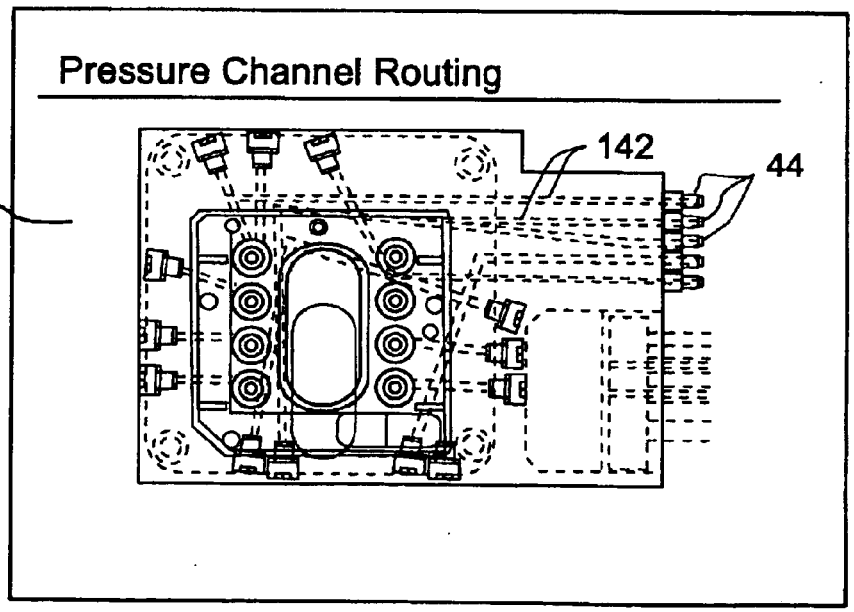

Referring now to FIGS. 11A and 11B, an exemplary manifold or chip interface structure 92' is illustrated in more detail. Exemplary manifold 92' is adapted to provide both hydrodynamic coupling and electrokinetic coupling between a microfluidic body and an associated controller, as described above. Electrical conduit passages 140 for coupling electrodes 94 to a system controller 22 (see FIG. 6) are illustrated in FIG. 1A. FIG. 11B illustrates manifold pressure transmission lumens 142 which provide fluid communication between fittings 44 and a microfluidic body interface surface 144 within manifold 92'. Manifold lumens 142 are illustrated in phantom.

Accurate control of the flow of fluids within a network of microfluidic channels can be quite challenging within even a relatively simple network of channels. More specifically, in many microfluidic applications, a variety of different fluids (with different characteristics) may be present in a single channel segment. As described above, where the hydro-resistance of each channel segment can be obtained, it may be possible to simulate and calculate the flow of fluids throughout the network for a given pressure configuration. Unfortunately, it can be quite difficult to accurately calculate viscosities (and, hence, resistances and flow rates) when several different buffers are used within a channel, often together with one or more different test fluid samples.

Fortunately, a relatively simple flow sensor can be provided to measure an actual flow within a channel of a microfluidic network. Where the measured flow results from a known driving force (such as a known pressure differential) can be determined, pressures to be applied at the fluid reservoirs so as to affect a desired flow condition may then be calculated.

Figure 12:
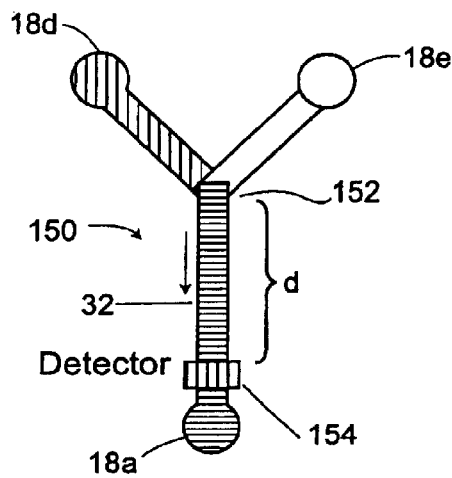
FIG. 12 schematically illustrates an exemplary microfluidic viscometer.

Referring now to FIG. 12, a relatively simple viscometer 150 makes use of a channel intersection 152 at a first location and a detector 154 at a second location to measure fluid flow characteristics. In general, a steady-state flow within a microfluidic channel 32 between intersection 152 and sensor 154 may be produced using a pressure differential between reservoirs 18, as described above. Intersection 152 may impose a signal on the steady-state flow by applying a pressure pulse to one or more of the reservoirs 18, by applying an electrokinetic pulse across intersection 152, or the like. The signal imposed at intersection 152 will often be in the form of a small flow perturbation, typically for a short duration. For example, where reservoir 18d includes a detectable dye, the flow perturbation or signal may comprise an increase or decrease in the dye concentration in the flow of microfluidic channel 32 from intersection 152 toward detector 154.

Detector 154 is downstream from intersection 152, and can be used to detect the arrival time of the signal, for example, as a peak or dip in the intensity of a fluorescent signal from the dye. Thus, the time difference between imposition of the signal at intersection 152 and sensing of the signal flow at detector 154 may be readily measured. Calling this time differential $\Delta t$, and knowing the distance along channel 32 between intersection 152 and detector 154, $\Delta d$, from the microfluidic network geometry, the flow rate Q can be calculated from the equation:

$$Q = A(\Delta d/\Delta t)$$

in which A is the cross-sectional area of the channel. This measured flow rate of a steady-state flow for a given initial driving force greatly facilitates calculation of an appropriate pressure configuration to achieve a desired flow.

Where viscosity is to be determined by the system of FIG. 12, reservoirs 18d and 18e coupled to channel 32 by intersection 152 may individually or in combination introduce fluid of known or unknown viscosity into the microfluidic channel at the intersection to provide a flow within the channel having an unknown total flow resistance. With channel 32 optionally containing only a trace amount of fluorescent dye (to inhibit any effect of the dye on the unknown overall viscosity), a substantially constant pressure configuration at ports 18 may drive flow from intersection 152 toward detector 154. This steady-state flow condition may be effected by a constant vacuum at reservoir 18a adjacent detector 154, positive pressures applied at reservoirs 18d, 18e adjacent intersection 152, or a combination of both. Regardless, the steady-state flow with a constant pressure differential will result in a volumetric flow rate Q in channel 32 which is linearly proportional to the pressure differential $\Delta P$ and inversely proportional to the fluid viscosity $\eta$ as follows:

$$Q = K\Delta P/\eta$$

K is a proportionality constant which depends on the geometry of the channel network. K can be calculated from the channel geometry, or can be determined through a calibration standard test, or the like.

A variety of alternative structures may be used to sense flow characteristics so as to apply a proper pressure configuration to generate a desired flow. For example, a signal may be imposed on a flow within a microfluidic channel by photobleaching of a fluorescent dye, rather than imposing a flow perturbation at a intersection. Alternative flow velocimetry approaches such as laser Dopler velocimetry, tracer particle videography, and the like are also possible. Using such techniques, a simple straight channel connecting a fluid supply reservoir and a waste fluid reservoir may suffice, with the fluid supply reservoir containing a fluid comprising a photobleachable fluorescent tracer dye or appropriate tracer particles.

As can be understood with reference to the calculations of flow rate Q above, sensors may also be used to determine alternative flow characteristics within a microfluidic channel, including flow rate, viscosity, the proportionality constant for a segment or network (by use of fluids having known and/or uniform viscosities) and/or other flow characteristics. In fact, in addition to providing a tool to study effective viscosity of two or more mixed fluids (of optionally unequal viscosity) still further measurements are possible. Mixing of DMSO and an acquiesce buffer can yield a non-monotonic viscosity-composition relationship. By applying different levels of pressure differential $\Delta P$ and measuring the flow rate Q, viscometer 150 could be used to establish a relationship of the effective viscosity during mixing as a function of mixing length. This information may be pertinent to chip design for tests which involve geometric dilution.

Where temperature dependency of viscosity is of interest, systems such as viscometer 150 can be coupled to a temperature control system comprising an external heater block in contact with the body defining the microfluidic channel network, by using joule heating to selectively control the temperature of fluids within the channel network, or the like.

In a still further alternative, a structure similar to viscometer 150 might be used to measure non-Newtonian viscosity. Non-Newtonian fluids have viscosities which are a function of the sheer rate experienced by the fluid. One example of a non-Newtonian fluid is a polymer solution containing high molecular weight molecules. A microfluidic viscometer similar to viscometer 150 of FIG. 12 might have a channel geometry and/or channel network intersection structure and/ or flow arranged so that the application of a pressure differential creates a range of sheer stresses so as to accurately measure such non-Newtonian viscosity.

Figure 13A:
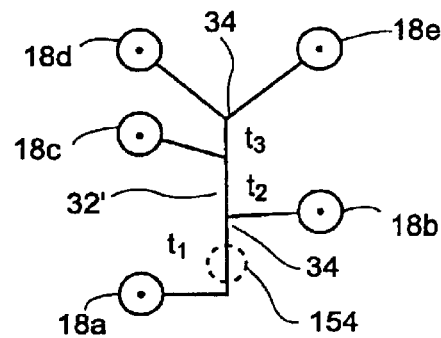
FIGS. 13A and 13B schematically illustrate a microfluidic network and method for imposing detectable signals on a microfluidic flow for measurement of flow characteristics which can be used to calculate pressures to affect a desired flow.
Figure 13B:
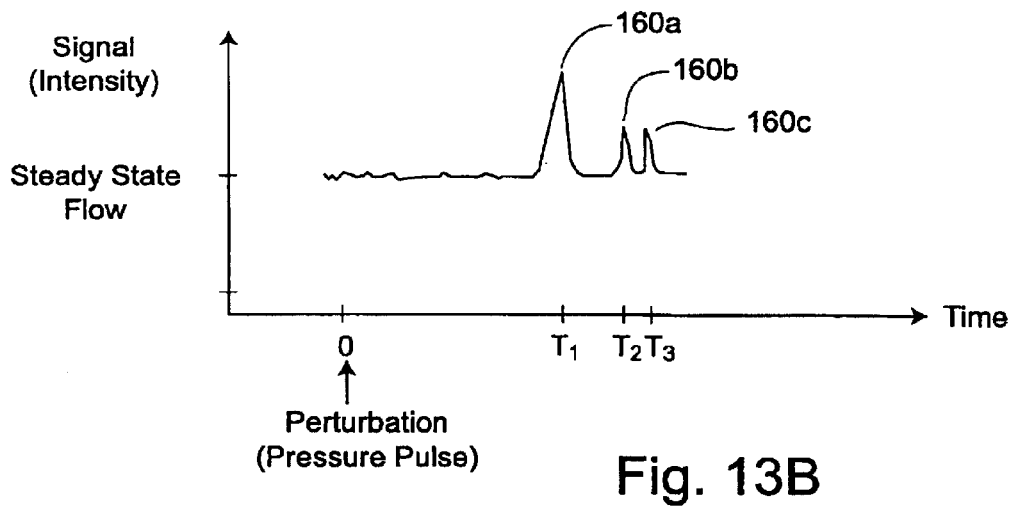
Figure 13C:
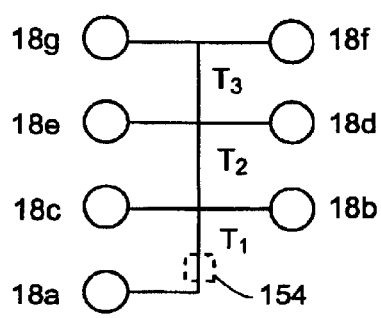

Real-time flow and viscosity measurements for microfluidic systems based on transient pressure pulse techniques can be further understood with reference to FIGS. 13A and 13B. A microfluidic network structure 30 with a single branch channel coupling each node to a main channel 32' is used. Each branch can be connected to a single reservoir 18 for a different buffer, sample, enzyme, or like. In the simplest embodiment, reservoir 18e at the end of the microfluidic channel network contains a dye solution to provide a detectable signal.

A steady flow can be directed toward reservoir 18a by applying initial pressures on wells 18. A short pressure pulse may be applied to well 18e and/or some or all of the other reservoirs of the microfluidic system. This pressure pulse will propagate substantially instantly to alter flow at some or all of the intersections 34 of network 30. This disturbance of the flow at the node points can change the dilution ratio from one or more of the side branches. After the pressure pulse, steady state flow is resumed.

As can be understood with reference to FIG. 13B, a time series of signals 160a, 160b, and 160c occur at times $T_1$, $T_2$, and $T_3$, respectively. The flow rate from some or all of the side branches may then be obtained from the difference of flow rates between successive node points. Once the flow rates of the branches have been obtained, as the pressures at reservoirs 18 are known, the resistances of the branch channels may then be calculated. From the known channel geometry, the viscosity of the solution in the side branches may also be determined. This information can then be fed back to the network model to derive the pressures for a desired flow rate from each reservoir.

Figure 14A:
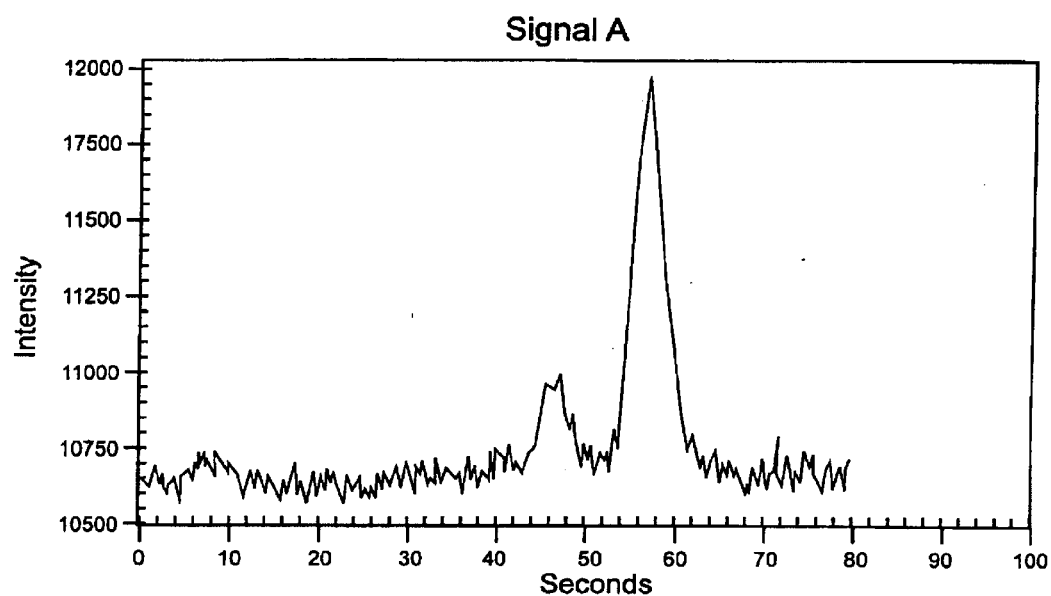
FIGS. 14A and 14B graphically illustrate flow characteristic signals which may be used to determine effective viscosity.
Figure 14B:
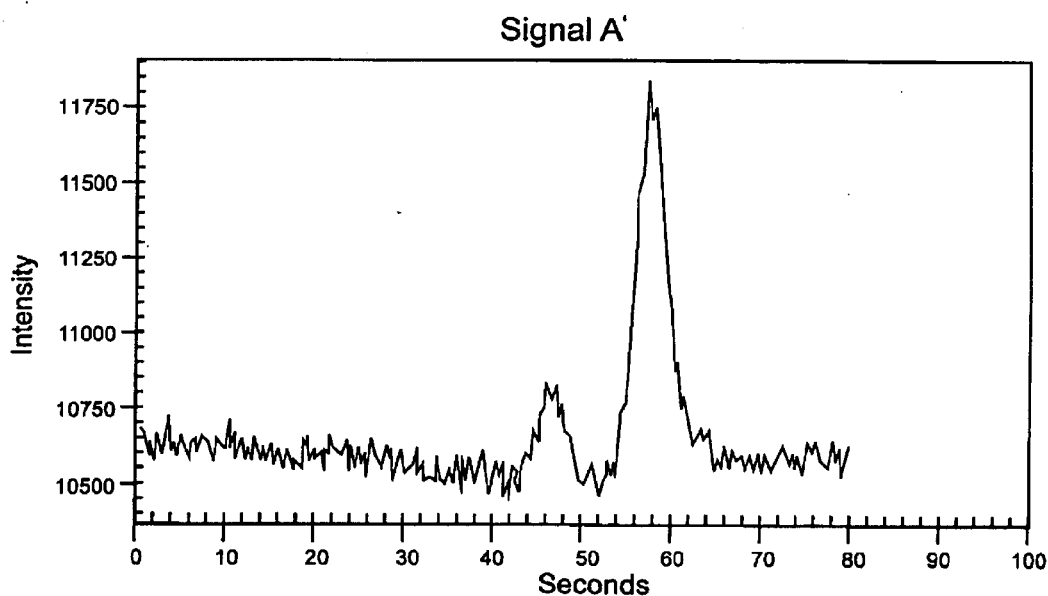

Referring now to FIGS. 14A and 14B, exemplary time signature data indicates that pressure pulse signals can effectively be imposed on the flow within a microfluidic system, and can accurately and repeatedly be sensed by a detector (such as an optical detector, or the like) for measurement of flow characteristics.

Hydrodynamic, electrokinetic, and other fluid transport mechanisms may be used in a variety of ways to provide specialized functions within a microfluidic system. For example, fluid mixtures such as biological fluid samples having particulates and/or cells in suspension within a liquid are often introduced into microfluidic systems. A particularly advantageous system and method for introducing a large number of samples into a microfluidic system is described in U.S. Pat. Nos. 5,779,868 and 5,942,443, the full disclosure of which is incorporated herein by reference. In that system, a vacuum may be used to draw a sequential series of fluid samples from the wells of a multi-well plate into a capillary tube in fluid communication with the microfluidic system.

In the above-described system, it may be desirable to maintain fluids at a substantially stationary location within the microfluidic channel, for example, during the time delay while a sample in a last well of a first multi-well plate is moved away from the capillary tube and before a sample in a first well of a second multi-well plate is in fluid communication with the capillary tube. Maintaining the fluids within the microfluidic channel at a substantially fixed location can avoid introducing significant amounts of air into the microfluidic system, which might interfere with its operation. In general, it may be desirable to maintain fluid mixtures at a given location within a microfluidic network for a wide variety of reasons.

Unfortunately, work in connection with the present invention has found that halting movement of some fluid mixtures within a microfluidic network may have significant disadvantages. Specifically, cell-based assays performed using a fluid mixture including cells suspended in a liquid are susceptible to sticking of the cells to the channel walls if flow is completely halted. Similarly, other fluids may deteriorate if flow within the channel is sufficiently low for a sufficient amount of time.

To avoid deterioration of fluid mixtures, the present invention can provide a small amplitude oscillatory movement of a fluid mixture so as to maintain the fluid mixture within a microfluidic channel. Modulator bank 14 is capable of providing a small amplitude oscillatory pressure such that there is no significant inflow or outflow of materials from the channel. This small amplitude oscillatory pressure will preferably be sufficient to continuously move the fluid mixture (and, for example, the cells within the liquid) continuously back and forth. The oscillation frequency should be high enough such that the instantaneous fluid mixture velocity is sufficiently high to avoid deterioration of the mixture, while amplitude should be small enough such that there is little or no unintended net transportation into or out of the channel from adjacent reservoirs, reservoirs and intersecting channels. Once the desired delay in fluid mixture movement has been provided it will often be desirable to flow an intervening liquid such as a buffer into the channel to help insure that unintended flows and/or mixtures at the channel ends have been flushed.

It should be noted that this small amplitude oscillatory motion may optionally be provided using electrokinetic forces, such as providing an alternating current, particularly if the alternating current is not harmful to cells or other components of the fluid mixture. It may also be beneficial to insure that cells in the channel do not lyse when subjected to the alternating current if electrokinetic forces are to be used to induce the oscillatory motion.

Figure 15:
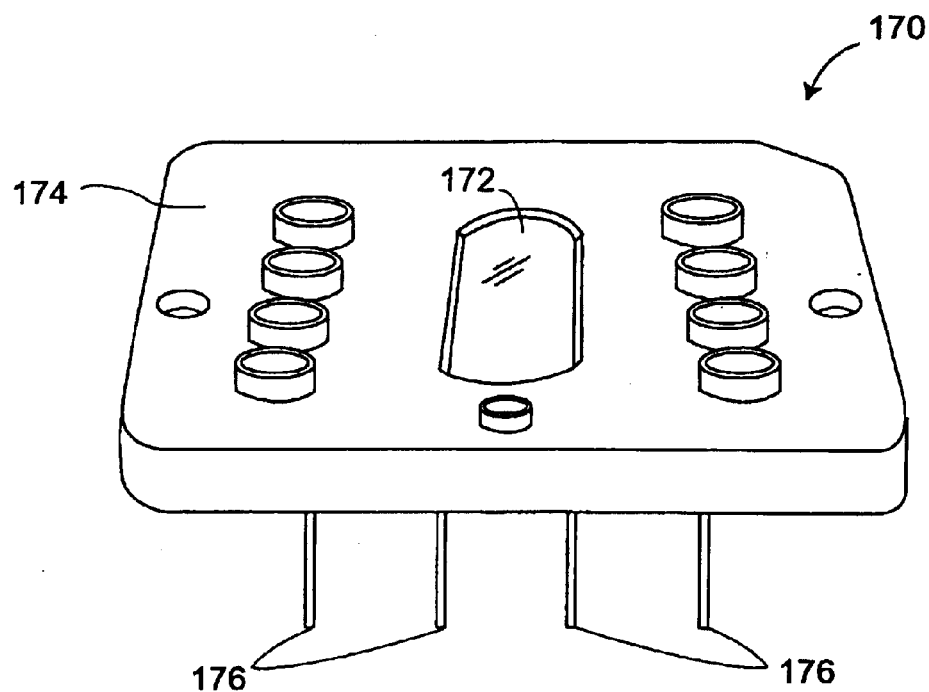
FIG. 15 is a perspective view of a microfluidic chip having a plurality of capillaries for spontaneous injection of fluids into the microfluidic network.

Referring now to FIG. 15, the systems and methods described above may optionally take advantage of a wide variety of pressure transient generators so as to initiate a flow perturbation. A multiple capillary assembly 170 includes a microfluidic body or chip 172 mounted a polymer interface housing 174. A plurality of capillaries 176 contain fluid introduction channels. As explained in detail in U.S. Pat. No. 6,149,787, the full disclosure of which is incorporated herein by reference, the capillary channels can be used to spontaneously inject fluids into the microfluidic network of chip 172 using capillary forces between the injected fluid and the capillary channels. Such spontaneous injection is sufficient to induce a pressure transient for measurement of hydrodynamic and/or electrokinetic flow. Such flow measurements allow the derivation of information regarding the properties of the chip, microfluidic network, and/or fluids.

Figure 16:
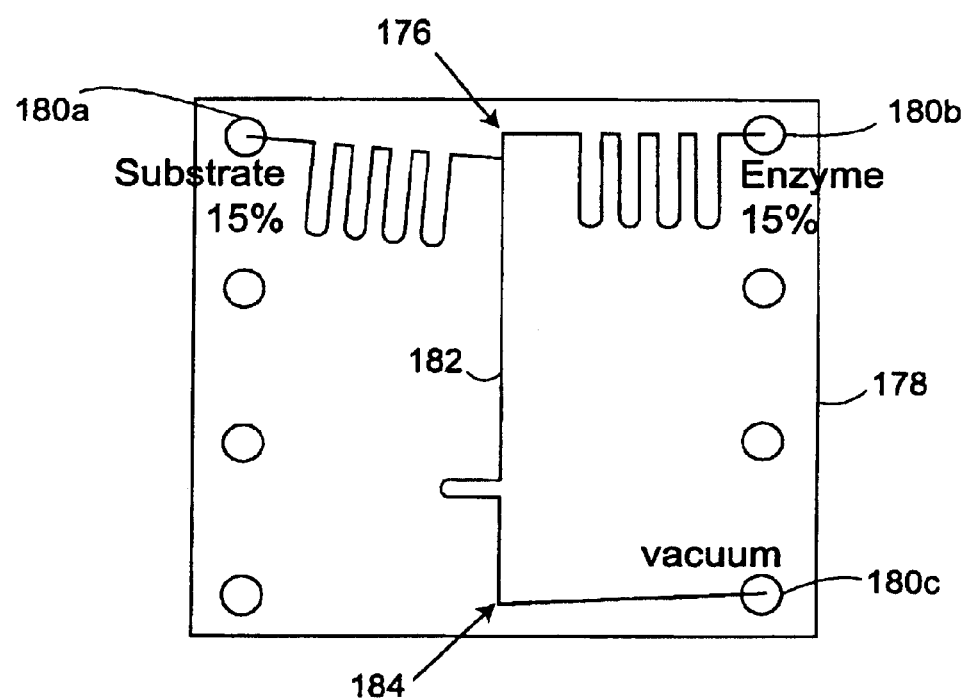
FIG. 16 is a top view of a simple microfluidic chip having a single capillary for spontaneous injection.

The use of multiple capillary assembly 170 is beneficial for parallel assays using a plurality of test samples, and the like. Referring now to FIG. 16, a simple chip 178 having a relatively straightforward microfluidic network may be used to understand the derivation of flow and/or chip properties from spontaneous injection. In many embodiments, the open end of capillary 176 will be placed in a fluid, typically by introducing the end of the capillary into a microtiter plate (or any other structure supporting one or more fluid test samples). This may be effected by moving the capillary 176 and chip 178 relative to the microtiter plate, by moving the microtiter plate relative to the capillary or by moving both structures relative to each other. Regardless, placing capillary 176 into a fluid results in spontaneous introduction of the fluid into the capillary channel. By applying a constant vacuum on at least one well of the microfluidic system, a steady flow may then be provided along a channel coupling the capillary to the well.

If, for example, a steady-state flow is induced from capillary 176, a substrate reservoir 180a, and/or an enzyme reservoir 180b toward a vacuum reservoir or waste well 180c along a channel 182, a flow perturbation can be initiated at intersection 186 between the capillary channel and the microfluidic network at the time the capillary is withdrawn out from the well containing the introduced fluid. This flow perturbation may, for example, comprise a change in composition of the flow progressing along channel 182 toward vacuum reservoir 180c. This change in composition may be sensed at a detection location 184 as, for example, a change in fluorescent intensity. Similar flow perturbations might be induced by applying other pressure transients at intersection 186, for example, when capillary 176 is introduced into the spontaneously injected fluid, or by applying a change in pressure using a pressure modulation pump as described above, again changing the composition of the flow within channel 182. By monitoring the property of the composition at detection point 184, progress of the perturbations may be detected. A time delay between initiation of the perturbation and their respective detections at the detection point, when combined with a known length of channel 182, can be used to determine a speed of the flow within the channel. From this actual, real-time speed, a variety of information regarding the fluid and/or network system may be determined.

Figure 16A:
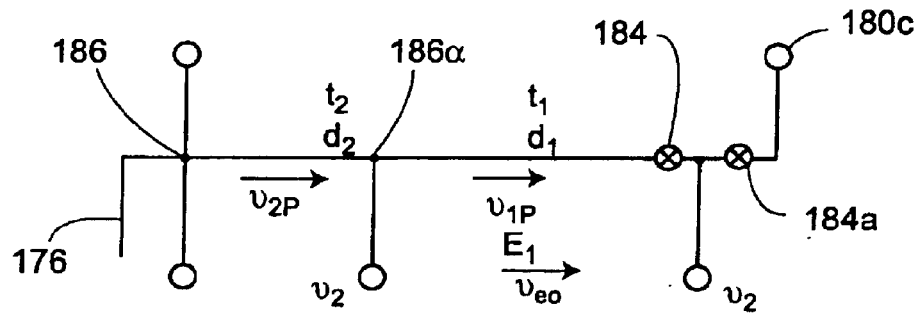
FIGS. 16A–16C graphically illustrate methods for monitoring progress of perturbations induced by spontaneous injection of fluids, for use in determining characteristics of a flow and/or microfluidic network.
Figure 16B:
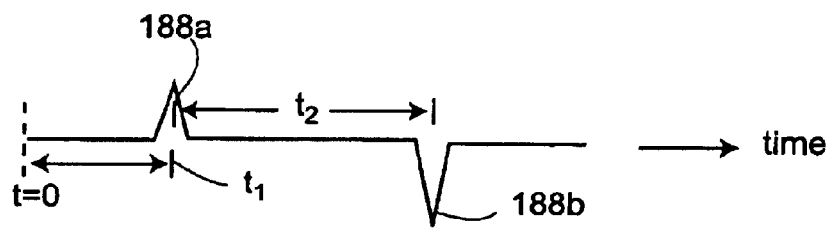

Referring now to FIGS. 16A and 16B, each time capillary 176 is dipped into and are removed from a fluid well, a perturbation will be generated at a capillary intersection 186 coupling the capillary channel with the microfluidic network. Additionally, as the pressure perturbation will propagate throughout the microfluidic network, another flow perturbation may be simultaneously initiated at a second intersection 186a downstream of the sipper intersection 186. If we assume that fluid is flowing from reservoirs affixed to the microfluidic network toward a vacuum reservoir 180c, the pressure transient applied by spontaneous injection at capillary 176 will alter the mixtures occurring at each intersection.

Where the channel lengths may be designated, and $\Delta d_1$, $\Delta d_2$ a time delay may be measured at detector 184 between initiation of the pressure transient (at t=0) and sensing of a first flow perturbation as a signal 188a at detector 184. The first signal 188a may be said to have occurred after a time delay of $\Delta t_1$, with this time being the time required for flow to propagate from the intersection immediately upstream of detector 184. A similar time delay $\Delta t_2$ will then be required for the flow to propagate from the second upstream intersection (186 in the simple network of FIG. 16A). Where the channel lengths between intersection are known, the various time delays can be used to determine the various fluid speeds between intersections. Where the channel cross-sections are known, this information can be used to determined contributions from branch channels to the flow volume, and the like, regardless of whether the flows throughout the microfluidic system are induced hydrodynamically, electrokinetically, electroosmotically, or the like.

Figure 16C:
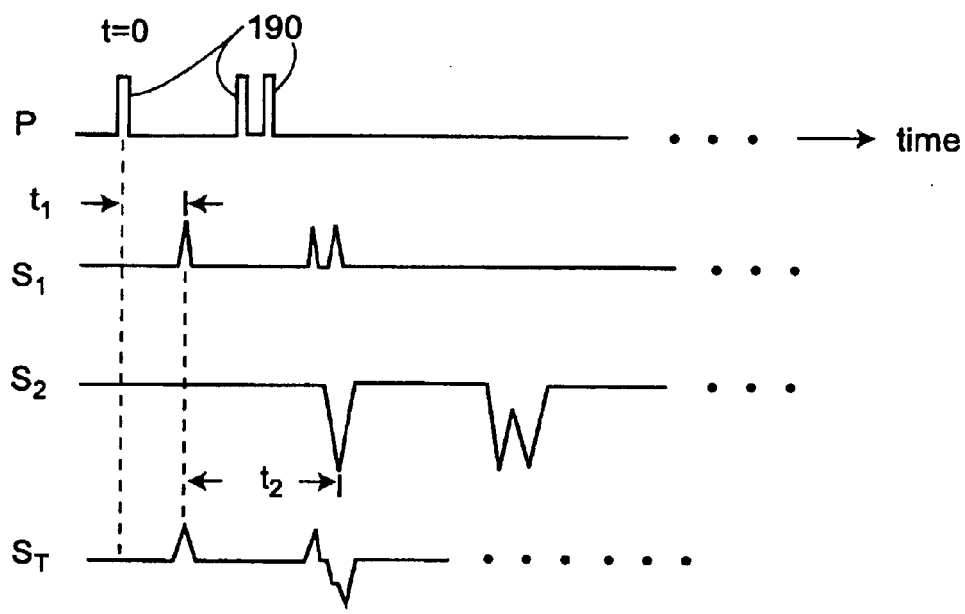

Referring now to FIG. 16C, capillary 176 may be dipped into and removed from a variety of fluids in a sequential series. P indicates pressure, $S_1$ is a signal indicating a flow perturbation caused at a first intersection by spontaneous injection into the capillary, and signals $S_2$ indicates a flow perturbation signal generated at a second intersection by the same spontaneous injection at the capillary. A series of pressure transients 190 will be generated by capillary 176 when the capillary is, for example, dipped into and removed from a dye, followed by dipping of the capillary into a buffer solution, followed dipping of the capillary into a first test substance well, and the like. This sequence of spontaneous injection events at capillary 176 may result in generation of a series of $S_1$ signals due to a series of flow perturbations at, for example, intersection 186a. Simultaneously, a series of second flow perturbation signals $S_2$ will also be generated at intersection 186, with detection of the second series following the first series by a time delay $\Delta t_2$ which is dependent on the speed of fluid within the network channels. The total signal $S_t$ measured at detector 184 will be a combination of this offset series of signals with the more immediate $S_1$ signals. Furthermore, the composition of the overall flow arriving at the detector may vary significantly with the different materials introduced by capillary 176. Regardless, by properly identifying the time delays between signals, flows between the nodes of the microfluidic system may be calculated.

Referring now to FIG. 16A, placing a detector 184a downstream of an electrode $v_1$ may facilitate measurements of electrically induced flow, such as electroosmotic flows induced by a differential voltage between $V_1$ and $V_2$. As described above, pressure perturbations will be initiated at the channel intersections, so that an initial signal may be generated at the detector from the downstream electrode $V_1$, followed by another signal generated at the upstream electrode $V_2$. Setting $\Delta t_1$, as the time delay between these electrode intersections and $\Delta t_2$, as the time delay for a subsequent signal generated by a reaction channel at intersection 186, and knowing the lengths of the channels $\Delta d_1$, $\Delta d_2$ we can calculate the electroosmotic EO flow as follows:

With voltage between the electrodes off, using only pressure to drive fluids within the network, we can determine velocities along the channels between nodes caused by pressure $v_{1P}$, $v_{2P}$ from:

$$\frac{\Delta t_2}{\Delta d_2} = v_{2p}$$

and $$\frac{\Delta t_1}{\Delta d_1} = v_{1p}$$

While leaving the same pressure differential on, the voltage differential may then be turned on, allowing us to calculate the electroosmotic flow velocity as follows:

$$\frac{\Delta t_2^1}{\Delta d_2} = v_{2p}$$

and $$\frac{\Delta t_1^1}{\Delta d_1} = v_{1p} + v_{eo};$$

which gives us $$v_{eo} = \frac{\Delta t_1^1 - \Delta t_1}{\Delta d_2}$$

Figure 19:
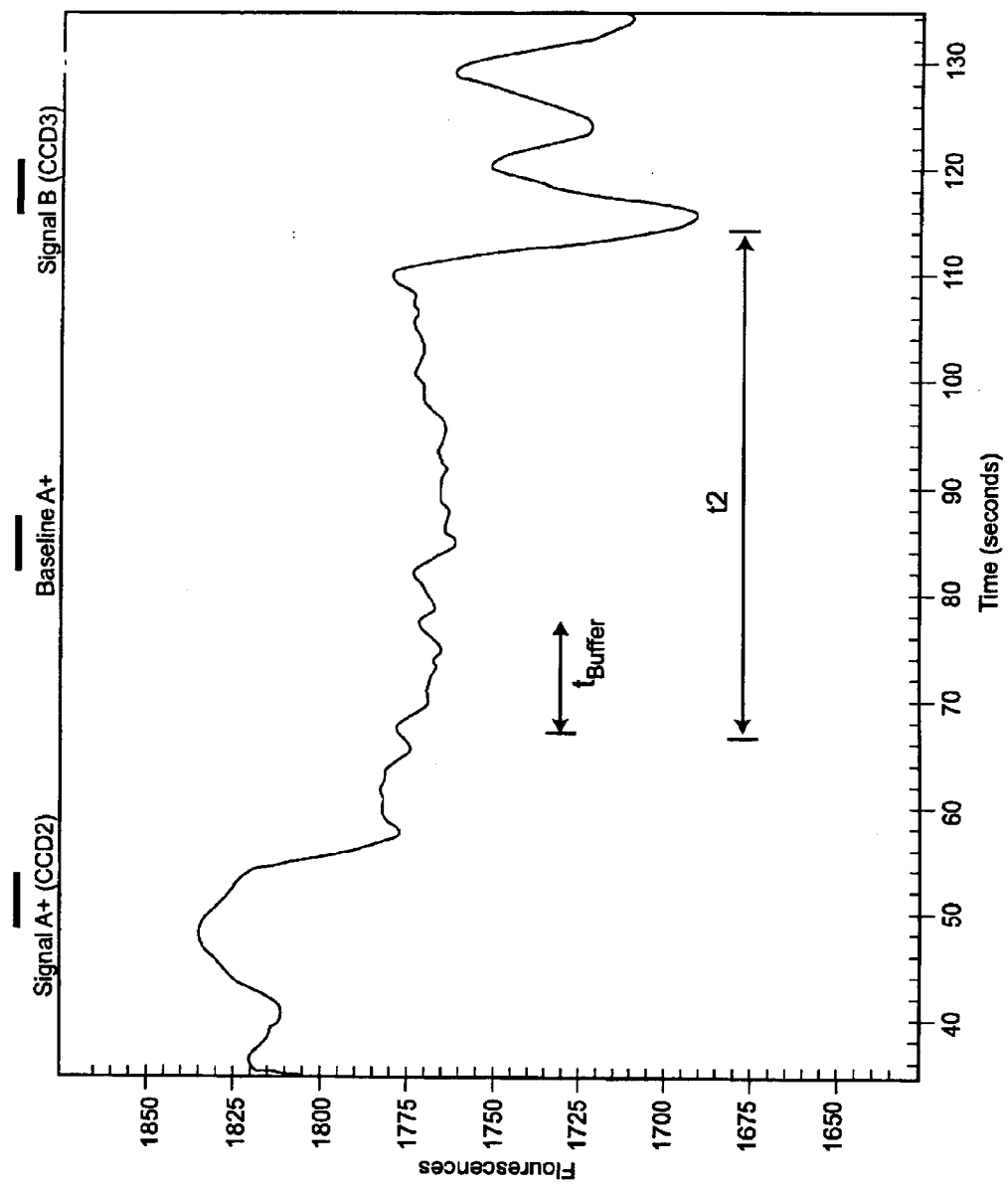
FIG. 19 graphically illustrates the detection of a perturbation generated at an intersection of microfluidic channels by spontaneous injection.

This electroosmotic velocity may then be used to calculate electroosmotic mobility using the equation:

$$\pi_{eo} = \frac{v_{eo}}{E_1},$$

in which $E_1$ is the electric field strength between the first and second voltages $V_1$, $V_2$. FIG. 19 graphically illustrates data from a detector or sensor from which the time delays discussed above may be taken.

The multiple capillary assembly and simplified capillary networks of FIGS. 15, 16 and 16A are examples of microfluidic devices which might benefit from monitoring of pressure induced flow perturbations for analysis and/or control of flows, quality control, and the like. Additional examples of microfluidic structures which may benefit from these techniques are illustrated in FIGS. 17A, 17B, 18A and 18B.

Figure 17A:
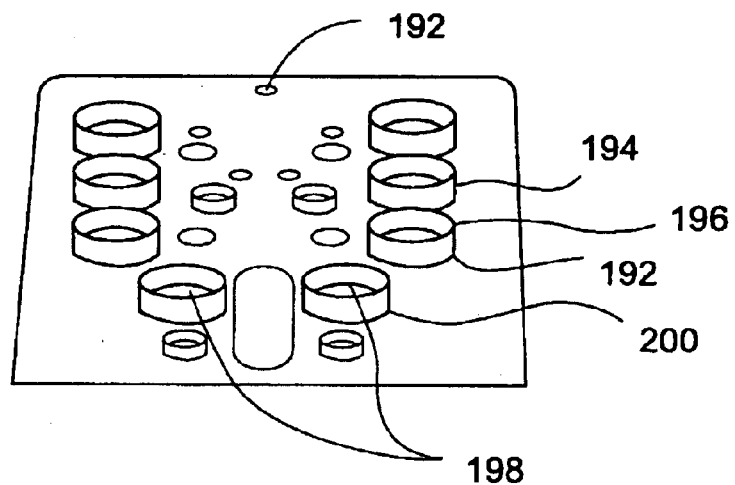
FIGS. 17A and 17B are perspective and plan view of fluorogenic multi-capillary chips.
Figure 17B:
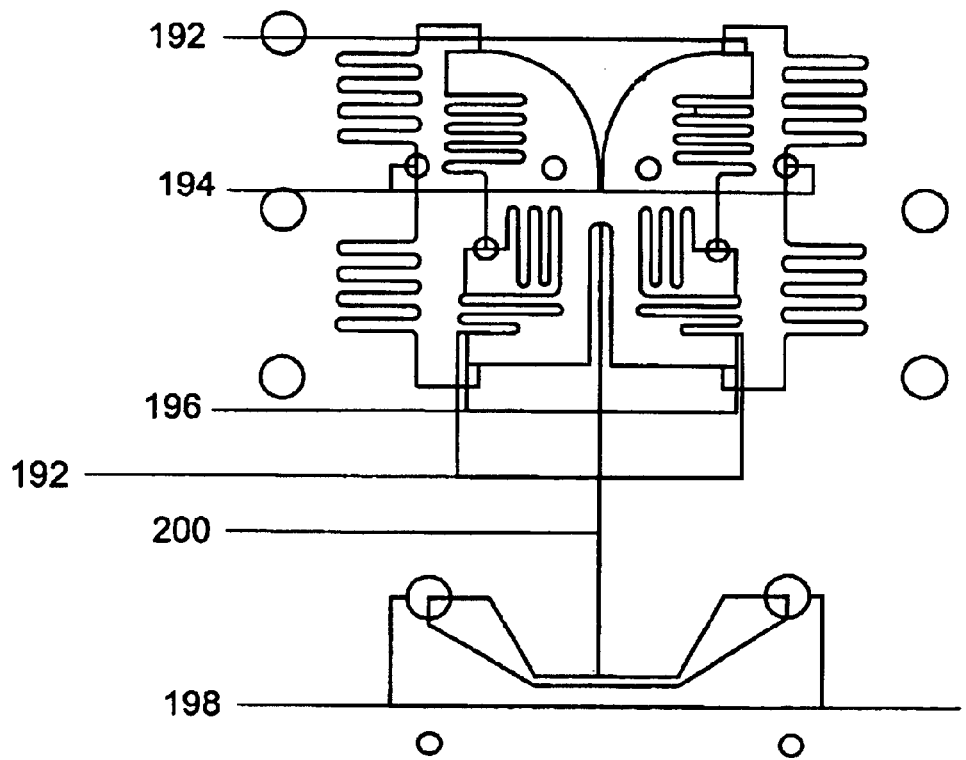
Figure 18A:
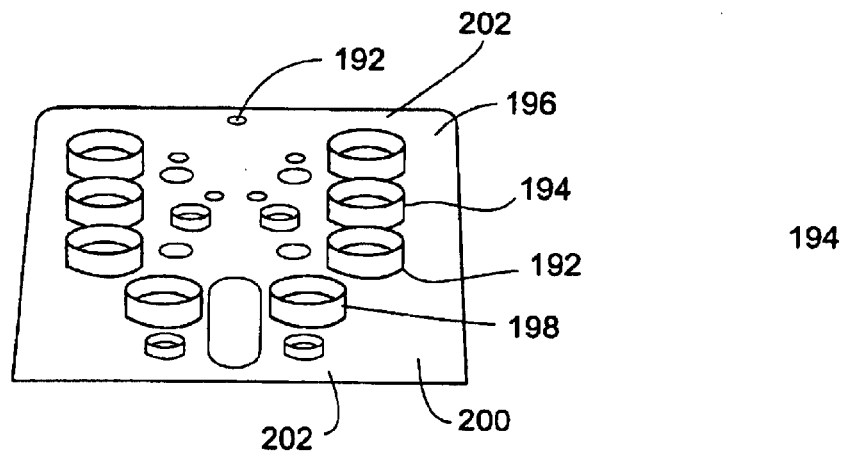
FIGS. 18A and 18B are perspective and plan view of a mobility-shift capillary chip.
Figure 18B:
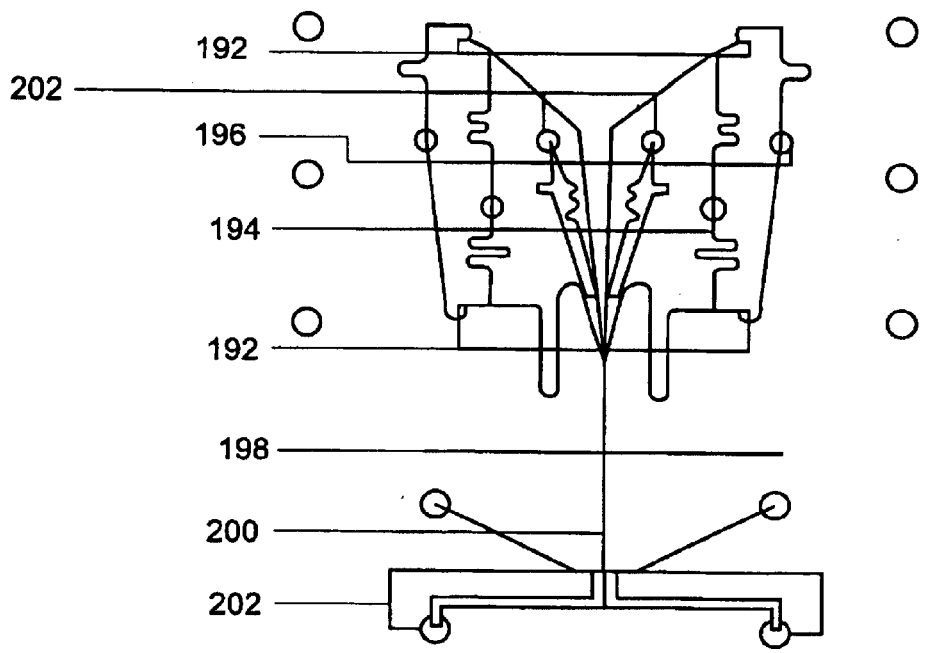

Referring now to FIGS. 17A and 17B, more complex microfluidic networks may include a plurality of capillary joints or intersections 192 and substrate wells or reservoirs 194, enzyme wells 196, wastewells 198, and the like. One or more detection or sensor windows or locations 200 may be provided for monitoring of propagation of the flow perturbations. The microfluidic assembly and network of FIGS. 17A and 17B may be useful for multi-capillary fluorogenic assays. A multi-capillary basic mobility-shift microfluidic assembly and network having similar structures is illustrated in FIGS. 18A and 18B. This structure also includes a plurality of electrode wells 202 for applying voltages to the microfluidic network, as described above.

While the exemplary embodiments have been described in some detail, by way of example and for clarity of example, a variety of modifications, changes, and adaptation will be obvious to those of skill in the art. Hence, the scope of the present invention is limited solely by the appended claims.

What is claimed is:

1. A microfluidic system comprising:
   a body defining a microfluidic channel network and a plurality of reservoirs in fluid communication with the network, the network including a channel;
   a plurality of pressure modulators, each pressure modulator providing a selectably variable pressure; and
   a plurality of pressure transmission lumens, the lumens transmitting the pressures from the pressure modulators to the reservoirs so as to induce a desired flow within the channel.

2. The microfluidic system of claim 1, wherein the channel has a resistance to the channel flow, and wherein the lumens transmit the pressures to the reservoirs with a lumen flow, resistance of the lumens to the lumen flow being significantly less than the channel resistance.

3. The microfluidic system of claim 1, wherein each pressure modulator is in fluid communication with an associated reservoir via an associated lumen, and further comprising a network flow controller coupled to the pressure modulators, the network controller transmitting signals to the pressure modulators, the pressure modulators independently varying the pressures in response to the signals so as to induce a channel flow within the channel.

4. The microfluidic system of claim 3, wherein the network controller comprises channel network data correlating the channel flows and the pressures from the pressure modulators.

5. The microfluidic system of claim 4, wherein the network controller calculates desired pressures from the pressure modulators in response to the network data and a desired flow in the channel.

6. The microfluidic system of claim 4, wherein the network comprises a plurality of microfluidic channels in fluid communication at channel intersections, the intersections and reservoirs defining nodes coupled by channel segments, and wherein the network data indicates correlations between flows in the channel segments and the plurality of pressures.

7. The microfluidic system of claim 6, further comprising a network data generator coupled to the network controller, the data generator comprising at least one member selected from the group consisting of a network flow model, a viscometer, and a network tester adapted to measure at least one parameter indicating the pressure-flow correlation.

8. The microfluidic system of claim 1, further comprising at least one pressure controller, and the pressure modulators varying the pressures in response to drive signals from the at least one pressure controller.

9. The microfluidic system of claim 8, further comprising a plurality of pressure sensors, each pressure sensor transmitting pressure signals to at least one pressure controller along a pressure feedback path in response to the pressures, wherein the pressure controllers transmit the drive signals to the pressure modulators in response to the pressure signals.

10. The microfluidic system of claim 8, wherein the pressure controllers comprise calibration data correlating the drive signals and the pressures.

11. The microfluidic system of claim 8, wherein the pressure modulators comprise pneumatic displacement pumps.

12. The microfluidic system of claim 1, wherein at least one sample test liquid is disposed in the channel network and pressure-transmission fluid is disposed in the lumens with a fluid/fluid pressure-transmission interface disposed therebetween.

13. The microfluidic system of claim 12, wherein the pressure-transmission fluid comprises a compressible gas.

14. The microfluidic system of claim 1, wherein the lumens compliantly couple the pressure modulators with the channel flow.

15. The microfluidic system of claim 1, wherein the plurality of pressure modulators comprise at least four independently variable pressure modulators.

16. The microfluidic system of claim 15, wherein the plurality of pressure modulators comprise at least eight independently variable pressure modulators.

17. The microfluidic system of claim 15, further comprising a pressure interface manifold releasably engaging the body, the manifold providing sealed fluid communication between the lumens and the reservoirs.

18. The microfluidic system of claim 1, further comprising a plurality of electrodes coupled to the network and an electrokinetic contoller coupled to the electrodes so as to induce electrokinetic movement of fluids within the network.

19. The microfluidic system of claim 1, wherein a difference between the pressures is significantly greater than a capillary pressure of fluids within the reservoirs.

20. A microfluidic method comprising:
transmitting a first plurality of pressures to an associated plurality of reservoirs using a plurality of pressure transmission systems;
inducing a first flow within a first microfluidic channel of a microfluidic network in response to the first pressures;
determining a second plurality of pressures so as to effect a desired second flow within the first microfluidic channel;
applying the determined second plurality of pressures with the pressure transmission systems; and
inducing the second flow within the first microfluidic channel with the second pressures.

21. The microfluidic method of claim 20, wherein the pressure transmission systems have resistances to pressure-transmission flows which are significantly less than a resistance of the microfluidic network to the pressure-induced flow during the flow inducing steps.

22. The microfluidic method of claim 20, wherein a first reservoir has a first fluid and a second reservoir has a second fluid, wherein the first and second reservoirs are coupled to the first channel, the first flow comprising a first solution with concentrations of the first and second fluids and the second flow comprises a second solution with concentrations of the first and second fluids different than the first solution, and wherein the determining step is performed so as to generate the second flow with the second solution.

* * * * *

UNITED STATES PATENT AND TRADEMARK OFFICE
CERTIFICATE OF CORRECTION

PATENT NO. : 6,915,679 B2
DATED : July 12, 2005
INVENTOR(S) : Chien et al.

It is certified that error appears in the above-identified patent and that said Letters Patent is hereby corrected as shown below:

Column 5,
Line 60, please delete "Dopler" and insert -- Doppler --.

Column 15,
Line 36, please delete "eleviate" and insert -- alleviate --.

Column 18,
Line 38, please delete "Dopler" and insert -- Doppler --.

Column 24,
Line 60, please delete "contoller" and insert -- controller --.

Signed and Sealed this

Thirteenth Day of September, 2005

JON W. DUDAS
*Director of the United States Patent and Trademark Office*